United States Patent
Yao et al.

(10) Patent No.: US 10,722,888 B2
(45) Date of Patent: Jul. 28, 2020

(54) DYNAMIC FORMATION OF NANOCHANNELS FOR SINGLE-MOLECULE DNA ANALYSIS

(71) Applicant: The Hong Kong University of Science and Technology, Hong Kong (CN)

(72) Inventors: Shuhuai Yao, Hong Kong (CN); Miao Yu, Hong Kong (CN); Youmin Hou, Hong Kong (CN)

(73) Assignee: The Hong Kong University of Science and Technology, Hong Kong (CN)

(*) Notice: Subject to any disclaimer, the term of this patent is extended or adjusted under 35 U.S.C. 154(b) by 114 days.

(21) Appl. No.: 15/577,676

(22) PCT Filed: Jun. 30, 2016

(86) PCT No.: PCT/IB2016/001045
§ 371 (c)(1),
(2) Date: Nov. 28, 2017

(87) PCT Pub. No.: WO2017/009710
PCT Pub. Date: Jan. 19, 2017

(65) Prior Publication Data
US 2019/0217295 A1    Jul. 18, 2019

Related U.S. Application Data

(60) Provisional application No. 62/193,542, filed on Jul. 16, 2015.

(51) Int. Cl.
*B01L 3/00* (2006.01)
*B01L 7/00* (2006.01)
(Continued)

(52) U.S. Cl.
CPC ... *B01L 3/502761* (2013.01); *B01L 3/502707* (2013.01); *B01L 7/52* (2013.01);
(Continued)

(58) Field of Classification Search
CPC ..... B01L 2200/0063; B01L 2300/0896; B01L 7/52; B01L 3/502761; B01L 2300/0861;
(Continued)

(56) References Cited

U.S. PATENT DOCUMENTS 7,217,562 B2    5/2007  Cao et al.
7,670,770 B2    3/2010  Chou et al.
(Continued)

FOREIGN PATENT DOCUMENTS

CA    2454570 A1    2/2003
CA    2482566 A1    12/2003
(Continued)

OTHER PUBLICATIONS

Wu et al "Complete plastic nanofluidic devices for DNA analysis via direct imprinting with polymer stamps" Lab Chip, 2011, 11: 2948-2989. (Year: 2011).*
(Continued)

*Primary Examiner* — Betty J Forman
(74) *Attorney, Agent, or Firm* — Saliwanchik, Lloyd & Eisenschenk

(57) ABSTRACT

Devices having nanochannels suitable for confinement and alignment of DNA molecules, as well as methods of fabricating the same and methods of using the same for DNA analysis, are provided. A device can include a dynamically-controlled, unified microchannel-nanochannel platform suitable for confinement and alignment of DNA molecules. The nanochannels can be reversibly formed within nanoslits formed in a deformable substrate or base layer.

14 Claims, 16 Drawing Sheets

(51) Int. Cl.
C12Q 1/6841 (2018.01)
G01N 33/487 (2006.01)

(52) U.S. Cl.
CPC ..... *C12Q 1/6841* (2013.01); *G01N 33/48721* (2013.01); *B01L 2200/0663* (2013.01); *B01L 2200/0668* (2013.01); *B01L 2300/021* (2013.01); *B01L 2300/08* (2013.01); *B01L 2300/0887* (2013.01); *B01L 2300/0896* (2013.01); *B01L 2300/123* (2013.01); *B01L 2400/0481* (2013.01); *B01L 2400/0655* (2013.01)

(58) Field of Classification Search
CPC ....... B01L 2400/0481; B01L 2200/143; B01L 2200/0668; B01L 2300/123; G01N 33/48721
See application file for complete search history.

(56) References Cited

U.S. PATENT DOCUMENTS

| | | | |
|---|---|---|---|
| 7,960,105 | B2 | 6/2011 | Schwartz et al. |
| 8,333,934 | B2 | 12/2012 | Cao et al. |
| 8,945,909 | B2 | 2/2015 | Takayama et al. |
| 2002/0022261 | A1* | 2/2002 | Anderson ........... B01F 11/0071 435/287.2 |
| 2002/0127736 | A1* | 9/2002 | Chou ................... B01L 3/5027 436/180 |
| 2007/0161028 | A1 | 7/2007 | Schwartz et al. |
| 2010/0159462 | A1 | 6/2010 | Takayama et al. |
| 2011/0201509 | A1 | 8/2011 | Tegenfeldt et al. |
| 2011/0275066 | A1 | 11/2011 | Schwartz et al. |
| 2012/0196376 | A1 | 8/2012 | Park et al. |
| 2013/0170026 | A1 | 7/2013 | Cohen et al. |
| 2013/0224736 | A1 | 8/2013 | Marie et al. |
| 2014/0030811 | A1 | 1/2014 | Cao et al. |
| 2014/0206555 | A1 | 7/2014 | Austin et al. |
| 2014/0238856 | A1 | 8/2014 | Ramsey et al. |
| 2014/0272958 | A1 | 9/2014 | Ramsey et al. |

FOREIGN PATENT DOCUMENTS

| | | |
|---|---|---|
| CA | 2787242 A1 | 7/2011 |
| CA | 2903481 A1 | 10/2014 |
| CN | 104312914 A | 1/2015 |
| EP | 1417474 | 5/2004 |
| EP | 1572860 | 9/2005 |
| EP | 2444157 A1 | 4/2012 |
| EP | 2484751 A2 | 8/2012 |
| EP | 2632592 | 9/2013 |
| WO | WO-2003/010289 A2 | 2/2003 |
| WO | WO-2003/106693 A3 | 12/2003 |
| WO | WO-2007/065025 A2 | 6/2007 |
| WO | WO-2008/079169 A2 | 7/2008 |
| WO | WO-2008/134363 A1 | 11/2008 |
| WO | WO-2010/042007 A1 | 4/2010 |
| WO | WO-2011/022650 A2 | 2/2011 |
| WO | WO-2011/038327 A1 | 3/2011 |
| WO | WO-2012/055415 A1 | 5/2012 |
| WO | WO-2012/056192 A1 | 5/2012 |
| WO | WO-2013/088098 A2 | 6/2013 |
| WO | WO-2014/164739 A1 | 10/2014 |

OTHER PUBLICATIONS

International Search Report in International Application No. PCT/IB2016/001045, filed Jun. 30, 2016.
Eriksson, E. et al., A microfluidic system in combination with optical tweezers for analyzing rapid and reversible cytological alterations in single cells upon environmental changes, Lab Chip, 2007, 7:71-76, The Royal Society of Chemistry 2007.
Heller, I. et al., STED nanoscopy combined with optical tweezers reveals protein dynamics on densely covered DNA, Nature Methods, Sep. 2013, 10(9):1-10, 2013 Nature America, Inc.
Chan, T. et al., A simple DNA stretching method for fluorescence imaging of single DNA molecules, Nucleic Acids Research, 2006, 34(17):1-6, 2006 The Author(s).
Otobe, K. et al., Behavior of DNA fibers stretched by precise meniscus motion control, Nucleic Acids Research, 2001, 29(22):1-6, 2001 Oxford University Press.
Labit, H. et al., A simple and optimized method of producing silanized surfaces for FISH and replication mapping on combed DNA fibers, BioTechniques, Dec. 2008, 45(6):649-658.
Bakajin, O. B. et al., Electrohydrodynamic Stretching of DNA in Confined Environments, Physical Review Letters, Mar. 23, 1998, 80(12):2737-2740, 1998 The American Physical Society.
Perkins, T. T. et al., Single Polymer Dynamics in an Elongational Flow, Science, Jun. 27, 1997, 276(5321):1-7.
Reisner, W. et al., DNA confinement in nanochannels: physics and biological applications, Rep. Prog. Phys., 2012, 75:1-35, 2012 IOP Publishing Ltd.
Persson, F. et al., Confinement Spectroscopy: Probing Single DNA Molecules with Tapered Nanochannels, Nano Letters, 2009, 9(4):1382-1385, 2009 American Chemical Society.
Reisner, W. et al., Statics and Dynamics of Single DNA Molecules Confined in Nanochannels, Physical Review Letters, May 2005, 94:196101-1-196101-4, 2005 The American Physical Society.
Huh, D. et al., Tuneable elastomeric nanochannels for nanofluidic manipulation, nature materials, Jun. 2007, 6:424-428, 2007 Nature Publishing Group.
Xu, B. et al., Large scale lithography-free nano channel array on polystyrene, Lab Chip, 2010, 10:2894-2901, The Royal Society of Chemistry 2010.
Waits, C. M. et al., Investigation of gray-scale technology for large area 3D silicon MEMS structures, Journal of Micromechanics and Microengineering, 2003, 13:1-9, 2003 IOP Publishing Ltd.
Berard, D. J. et al., Convex lens-induced nanoscale templating, PNAS, Sep. 16, 2014, 111(37):13295-13300.
Reinhart, W. F. et al., Entropic depletion of DNA in triangular nanochannels, Biomicrofluidics, 2013, 7:024102-1-024102-9, 2013 American Institute of Physics.
Min, S. K. et al., Fast DNA sequencing with a graphene-based nanochannel device, Nature Nanotechnology, Mar. 2011, 6:162-165, 2011 Macmillan Publishers Limited.
Shendure, J. et al., Next-generation DNA sequencing, Nature Biotechnology, Oct. 2008, 26(10):1135-1145, 2008 Nature Publishing Group.
Treangen, T. J. et al., Repetitive DNA and next-generation sequencing: computational challenges and solutions, Nature Reviews Genetics, 2012, 13(1):1-21.
Ley, T. J. et al., DNA sequencing of a cytogenetically normal acute myeloid leukaemia genome, Nature, Nov. 6, 2008, 456:66-72, 2008 Macmillan Publishers Limited.
Levy-Sakin, M. et al., Beyond sequencing: optical mapping of DNA in the age of nanotechnology and nanoscopy, Current Opinion in Biotechnology, 2013, 24:690-698, 2013 Elsevier Ltd.
Cheeseman, K. et al., A Diagnostic Genetic Test for the Physical Mapping of Germline Rearrangements in the Susceptibility Breast Cancer Genes BRCA1 and BRCA2, Human Mutation, 2012, 33(6):998-1009, 2012 Wiley Periodicals, Inc.
Lam, E. T. et al., Genome mapping on nanochannel arrays for structural variation analysis and sequence assembly, Nature Biotechnology, Aug. 2012, 30(8):771-777, 2012 Nature America, Inc.
Persson, F. et al., DNA in nanochannels-directly visualizing genomic information, Chemical Society Reviews, 2010, 39:985-999, The Royal Society of Chemistry 2010.
Reisner, W. et al., Single-molecule denaturation mapping of DNA in nanofluidic channels, PNAS, Jul. 27, 2010, 107(30):13294-13299.
Park, S. et al., A method for nanofluidic device prototyping using elastomeric collapse, PNAS, Sep. 15, 2009, 106(37):15549-15554.
Matsuoka, T. et al., Nanoscale Squeezing in Elastomeric Nanochannels for Single Chromatin Linearization, Nano Letters, 2012, 12:6480-6484, 2012 American Chemical Society.

(56) References Cited

OTHER PUBLICATIONS

Jo, K. et al., A single-molecule barcoding system using nanoslits for DNA analysis, PNAS, Feb. 20, 2007, 104(8):2673-2678, 2007 The National Academy of Sciences of the USA.

Mak, A. C. Y. et al., Genome-Wide Structural Variation Detection by Genome Mapping on Nanochannel Arrays, Genetics, Jan. 2016, 202:1-65, 2016 the Genetics Society of America.

Freitag, C. et al., Visualizing the entire DNA from a chromosome in a single frame, Biomicrofluidics, 2015, 9:044114-1-044114-10, Author(s) 2015.

Marie, R. et al., Integrated view of genome structure and sequence of a single DNA molecule in a nanofluidic device, PNAS, Mar. 26, 2013, 110(13):4893-4898.

Mahshid, S. et al., Development of a platform for single cell genomics using convex lens-induced confinement, *Lab Chip*, 2015, 15:3013-3020, The Royal Society of Chemistry 2015.

Østergaard, P. F. et al., DNA barcoding via counterstaining with AT/GC sensitive ligands in injection-molded all-polymer nanochannel devices, *Analyst*, 2013, 138:1249-1255, The Royal Society of Chemistry 2013.

Menard, L. D. et al., Fabrication of Sub-5 nm Nanochannels in Insulating Substrates Using Focused Ion Beam Milling, Nano Letters, 2011, 11:512-517, 2010 American Chemical Society.

Mills, K. L. et al., Instantaneous fabrication of arrays of normally closed, adjustable, and reversible nanochannels by tunnel cracking, *Lab Chip*, 2010, 10:1627-1630, The Royal Society of Chemistry 2010.

Cao, H. et al., Gradient nanostructures for interfacing microfluidics and nanofluidics, Applied Physics Letters, Oct. 14, 2002, 81(16):1-4, 2002 American Institute of Physics.

Kim, B. C., Fracture-based fabrication of a size-controllable micro/nanofluidic platform for mapping of DNA/chromatin, pp. 1-153, Byoung Choul Kim.

Angeli, E. et al., Micro and nanofluidic platforms for advanced diagnostics, Edorium Journal of Nanotechnology, 2014, 1:1-7.

Fernandez-Cuesta, I. et al., Fabrication of fluidic devices with 30 nm nanochannels by direct imprinting, Journal of Vacuum Science & Technology B, 2011, 29(6):1-8, 2011 American Vacuum Society.

Napoli, M. et al., Nanofluidic technology for biomolecule applications: a critical review, *Lab Chip*, 2010, 10:957-985, The Royal Society of Chemistry 2010.

\* cited by examiner

DYNAMIC FORMATION OF NANOCHANNELS FOR SINGLE-MOLECULE DNA ANALYSIS

CROSS-REFERENCE TO RELATED APPLICATIONS

This application is the U.S. national stage application of International Patent Application No. PCT/IB2016/001045, filed Jun. 30, 2016, which claims the benefit of U.S. Provisional Application Ser. No. 62/193,542, filed Jul. 16, 2015, the disclosures of each of which are incorporated herein by reference in their entirety.

BACKGROUND OF INVENTION

DNA contains the basic blueprint of almost all living organisms, and understanding the information of DNA molecules is a crucial topic for biological research and biomedical engineering. However, in a bulk solution, DNA molecules are typically coiled up, which can make analysis difficult. To reveal the genomic information of DNA molecules, various approaches have been investigated to stretch the tangled DNA molecules, such as optical and magnetic tweezers, surface-based combing, and extension in hydrodynamic flow.

DNA linearization is the prerequisite and critical step in single-molecule DNA analysis. When confined in a nanochannel, a coiled DNA molecule naturally stretches out as a combined result of its elastic properties and the excluded volume effect, depending on the dimensions of the nanochannel. Compared with other competing approaches, DNA stretching by nanoconfinement allows for a uniform elongation where the confined DNA molecule is exposed to the same confinement force and provides for long observation time of DNA in its unraveled state. The feature size of nanofluidic devices for DNA manipulation are usually required to be comparable or smaller than the persistence length of double-strand DNA (i.e., on the order of 10 to 100 nanometers) and uniform over tens to hundreds of micrometers and even centimeters. Conventional methods for patterning sub-100 nm channels use scanning beam lithography, where a beam is scanned across a substrate, such as in electron beam lithography (EBL) and focused ion beam lithography (FIB). However, conventional nanolithography techniques are usually very expensive and time consuming, and the devices are generally not reusable once contaminated. Alternative non-lithographic methods based on nanocracking can reduce the cost of device, but the uniformity of the resulting nanochannel arrays is relatively low. Also, the step interface between the loading microchannels and the stretching nanochannels in conventional nanofluidic devices poses a large entropic barrier, where the coiled DNA molecules clog at the junction. Although gray-scale lithography can harness this entropic force by creating a gradient at the interface, the mask design process is complicated and the fabrication of a refined gradient structure remains challenging. A convex lens-induced confinement (CLIC) platform can utilize the curved surface of a convex lens to locally deform a flexible coverslip above the micro/nano-structured surface, but expensive EBL is still needed to produce nanochannels on the glass surface of the CLIC platforms, and the depth of the generated nanochannels are not uniform. In addition, the nanochannels in conventional nanofluidic devices are essentially directly bonded. High pressure or electric fields are required for surface passivation, sample transport, and buffer refreshment due to the high hydraulic resistance of the nanochannels.

Existing DNA analysis methods and devices have many problems, and several challenges remain in order to reduce the cost of nanofluidic devices and improve the performance for DNA analysis with such devices.

BRIEF SUMMARY

Embodiments of the subject invention provide novel and advantageous devices having nanochannels suitable for confinement and alignment of DNA molecules (e.g., for single-molecular analysis), as well as methods of fabricating the same and methods of using the same for DNA analysis. A device can include a dynamically-controlled, unified micro-channel-nanochannel platform suitable for confinement and alignment of DNA molecules. The device can include: (a) a sample microchannel having a geometric feature (e.g., a semicircular cross-section) and a stiffness feature (e.g., collapsible material) that promote a desired frequency of microchannel collapse and the resulting uniform closure; (b) one or more nanostructures (e.g. open structure(s) with a depth less than or equal to 100 nm) on the roof or bottom surface of the sample microchannel; and (c) a control microchannel located on the top or bottom of the sample microchannel to control the collapse of the interlayer and create nanochannel(s) enclosed by a portion of the collapsed interlayer and the bottom of the sample microchannel.

The nanochannels can be formed within nanoslits formed in a substrate, which can be deformable, such as a deformable polymer (e.g., polydimethylsiloxane (PDMS)). Pneumatic control (e.g., pneumatic microvalve control), along with deformation of the substrate (e.g., PDMS), can result in production of uniform nanochannels (e.g., uniform triangular nanochannels) having a size of tens of nanometers and a length of submillimeter. The nanoslits can be formed using lithography (e.g., low-cost soft-lithography). The effective size of the nanochannels can be continuously adjusted by the applied pressure. The microvalve deformation can naturally create a gradient in depth and smoothly adjoin the formed nanochannels and the microchannel(s) for DNA loading, which effectively eliminates the problem of DNA stacking at the entrance of the nanochannels and obviates the need for high pressure or electric fields during the DNA introduction. Unlike conventional direct-bonded nanochannels, the sample channel can recover in microscale when the pressure is released, facilitating buffer exchange, sample loading, and surface passivation. Embodiments of the subject invention can be used for affordable DNA mapping and/or profiling instruments, for example, for genetic/epigenetic research, clinical diagnosis, and forensic identification.

The rapid development of nanofabrication techniques offers a new way to manipulate and analyze single DNA molecules. When confined in a nanochannel, a coiled DNA molecule naturally stretches out as a combined result of its elastic properties and the excluded volume effect, depending on the dimensions of the nanochannel. Compared with other competing approaches, DNA stretching by nanoconfinement allows a uniform elongation where the confined DNA molecule is exposed to the same confinement force and provides for long observation time of DNA in its unraveled state. By parallelizing the nanochannels and coupling them with well-developed microfluidics, tens and hundreds of prolonged DNA molecules can be analyzed simultaneously, allowing rapid acquisition of statistics, high reproducibility, and easy automation.

In an embodiment, a device for macromolecule (e.g., DNA or protein) analysis can comprise: a sample microchannel having a cross-section and stiffness configured to allow microchannel collapse with uniform (or approximately uniform) closure; at least one open nanostructure formed on the roof or bottom surface of the sample microchannel, wherein the at least one open nanostructure has a depth of 100 nm or less; and a control microlayer (e.g., a pneumatic microvalve) disposed above or below the sample microchannel and configured to control collapse of the sample microchannel, an interlayer of the sample microchannel being disposed between the control microchannel and an open portion of the sample microchannel. The device can be configured such that, when pressure is applied to the interlayer by the control microchannel, the interlayer is forced into the at least one nanostructure and makes contact with a bottom surface thereof, thereby forming nanochannels within the nanostructure.

In another embodiment, a device for DNA analysis can include: a deformable base layer having at least one nanoslit, with a depth of 900 nanometer (nm) or less (and optionally a length of less than 1 millimeter (mm) and/or a width of 1 micron or more), formed therein in a channel region thereof; and an interlayer disposed on the base layer such that a sample microchannel is formed between a portion of the interlayer and the channel region of the base layer. The device can be configured such that, when pressure is applied to the interlayer, the interlayer is forced into the at least one nanoslit and makes contact with a bottom surface thereof, thereby forming nanochannel within the nanoslit. Each nanochannel can have a triangular cross-section when viewed lengthwise.

In another embodiment, a method of analyzing DNA utilizing a device as described herein can include the steps of: providing a DNA molecule to the at least one nanoslit (or open nanostructure); and applying pressure to an upper surface of the interlayer such that the sample microchannel collapses and the interlayer is forced into the nanoslit (or open nanostructure), thereby forming nanochannels therein. The DNA molecule can be stretched and linearized within a nanochannel of the nanoslit (or open nanostructure) when the microchannel collapses due to the pressure applied to the interlayer. The pressure applied to the upper surface of the interlayer can include pneumatically applying pressure (e.g., using a microvalve) to the upper surface of the interlayer.

In yet another embodiment, a method of fabricating a DNA analysis device can include the steps of: forming a first master template for a nanostructured surface, the first master template having at least one nanoslit formed therein; forming a second master template for a sample microchannel; depositing a photoresist material on the second master template; depositing a first deformable material on the first master template; removing the first master template from the first deformable material, thereby forming a base layer of the first deformable material having the at least one nanochannel formed therein in a channel region thereof; depositing a second deformable material on the second master template and the photoresist material; removing the second master template and the photoresist material from the second deformable material, thereby forming an interlayer of the second deformable material having a sample microchannel formed therein in a shape of the photoresist material; and disposing the interlayer on the base layer such that the at least one nanoslit of the base layer faces the interlayer, and the sample microchannel is disposed facing the base layer and over the channel region of the base layer. The resulting device can be configured such that, when pressure is applied to the interlayer, the interlayer is forced into the at least one nanoslit and makes contact with a bottom surface thereof, thereby forming nanochannels within the nanoslit.

DETAILED DESCRIPTION

Figure 1A:
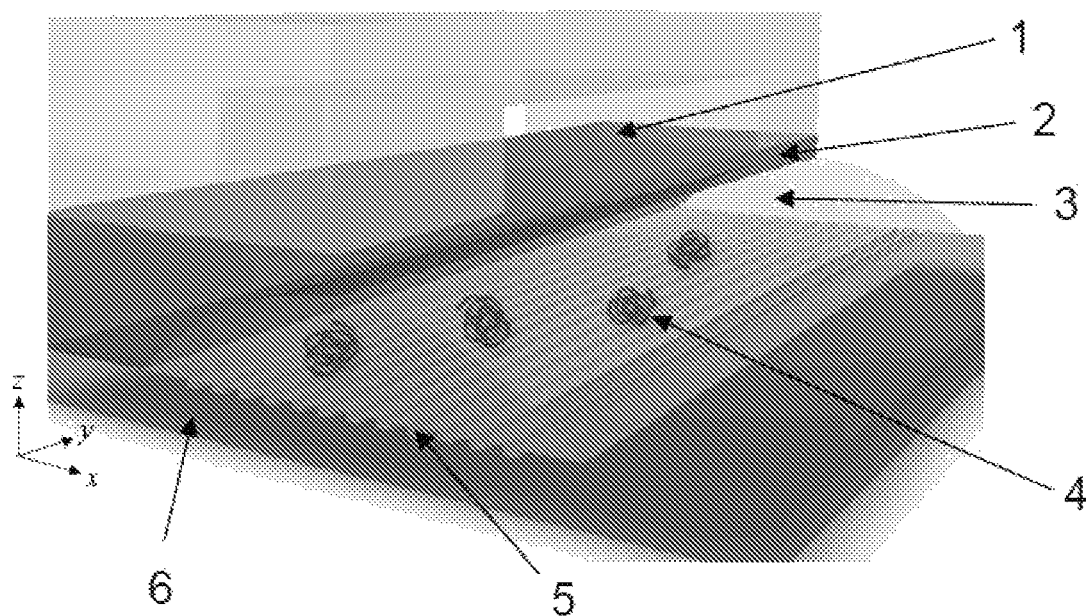
FIG. 1A shows a schematic view of DNA solution transport in recovered microchannels when the interlayer is not deformed, according to an embodiment of the subject invention.

Embodiments of the subject invention provide novel and advantageous devices having one or more nanochannels suitable for confinement and alignment of DNA molecules (e.g., for single-molecular analysis), as well as methods of fabricating the same and methods of using the same for DNA analysis. A device can include a dynamically-controlled, unified microchannel-nanochannel platform suitable for confinement and alignment of DNA molecules. The one or more nanochannels can be formed in a substrate, which can be deformable, such as a deformable polymer (e.g., polydimethylsiloxane (PDMS)). Pneumatic control (e.g., pneumatic microvalve control), along with deformation of the substrate (e.g., PDMS), can result in one or more uniform nanochannels (e.g., uniform triangular nanochannels) having a width of tens of nanometers and a length of submillimeter can be produced. This can be done using lithography (e.g., low-cost soft-lithography). The effective size (e.g., width) of the one or more nanochannels can be continuously adjusted by the applied pressure. The microvalve deformation can naturally create a gradient in depth and smoothly adjoin the formed nanochannel(s) and the microchannel(s) for DNA loading, which effectively eliminates the problem of DNA stacking at the entrance of the nanochannel(s) and obviates the need for high pressure or electric fields during the DNA introduction. Unlike conventional direct-bonded nanochannels, the sample channel can recover in microscale when the pressure is released, facilitating buffer exchange, sample loading, and surface passivation. Embodiments of the subject invention can be used for affordable DNA mapping and/or profiling instruments, for example, for genetic/epigenetic research, clinical diagnosis, and forensic identification.

The term nanoslit refers to a channel with one physical dimension (e.g., the depth) equal to or less than 100 nm; the width of the nanoslit can be micro-sized (i.e., can be greater than 100 nm wide). The term nanochannel refers to a channel with two physical dimensions (both width and depth) equal to or less than 100 nm.

In many embodiments, uniform triangular nanochannels having a width of tens of nanometers and a length of submillimeter can be dynamically formed and adjusted by control of a pneumatic microvalve on a deformable substrate (e.g., a polymer such as PDMS). The fabrication methods of embodiments of the subject invention can reduce the cost and complexity of nanochannels compared to those patterned by electron beam lithography (EBL) or ion beam milling. The formed nanochannels can be size-tunable, highly uniform, and sufficiently long. They can be well-suited for linearization of DNA molecules spanning from several hundred kbp (kilo-base pairs, or thousands of base pairs) up to the Mbp (mega-base pairs, or millions of base pairs) range. The deformed substrate can naturally create a gradient in depth and smoothly adjoin the formed nanochannels and the microchannels for DNA loading. This can effectively inhibit or even prevent DNA stacking at the entrance of the nanochannels, which is a major challenge faced by most conventional nanochannel devices. In addition, nanochannel fabrication of embodiments of the subject invention can be compatible with microfluidics for upstream sample preparation and downstream sample extraction, readily applicable for automated high-throughput assays.

Conventionally, to achieve dimension below a micron, the width of a channel is defined by expensive nanolithography techniques, such as electron beam lithography or focused ion beam, and the depth can be defined by controlling the etching time (e.g., using reactive ion etching (RIE)). When fabricating nanoslits, the width can be defined by conventional low-cost lithography, and the depth by controlling the etching time. Thus, the cost of nanoslit fabrication is much lower than that of nanochannels. In many embodiments of the subject invention, low-cost nanoslits can first be fabricated. Then, a pair of nanochannels can be created at the edge of each nanoslit by closing the top layer of the channel. The width and the depth of the created nanochannels are determined by the depth of the nanoslits and the control pressure, which is irrelevant to the width of the nanoslits. The created nanochannels can then be used for DNA analysis.

Compared with conventional nanochannels fabricated in silicon or quartz and using expensive lithography methods, devices of embodiments of the subject invention (e.g., a PDMS chip) can largely reduce the fabrication cost. The uniformity of the nanochannels can ensure uniform stretching of DNA molecules and accurate mapping results in DNA analysis in nanochannels. Compared with conventional high-cost nanolithographic fabrication methods, nanochannels of embodiments of the subject invention show the same good uniformity. A steep entropic barrier needs to be overcome at the interface between the microchannels to nanochannels for DNA sample loading in nanofluidic devices. In the unified micro-nanochannel design according to embodiments of the subject invention, the depth differences between the formed nanochannels and adjoining microchannels are smoothly bridged by the curved edge of the microvalve, which facilitates DNA molecules entering the nanochannels. This design is compatible with microfluidics for upstream sample preparation and downstream sample extraction, making it readily compatible with automated high-throughput assays.

Figure 1B:
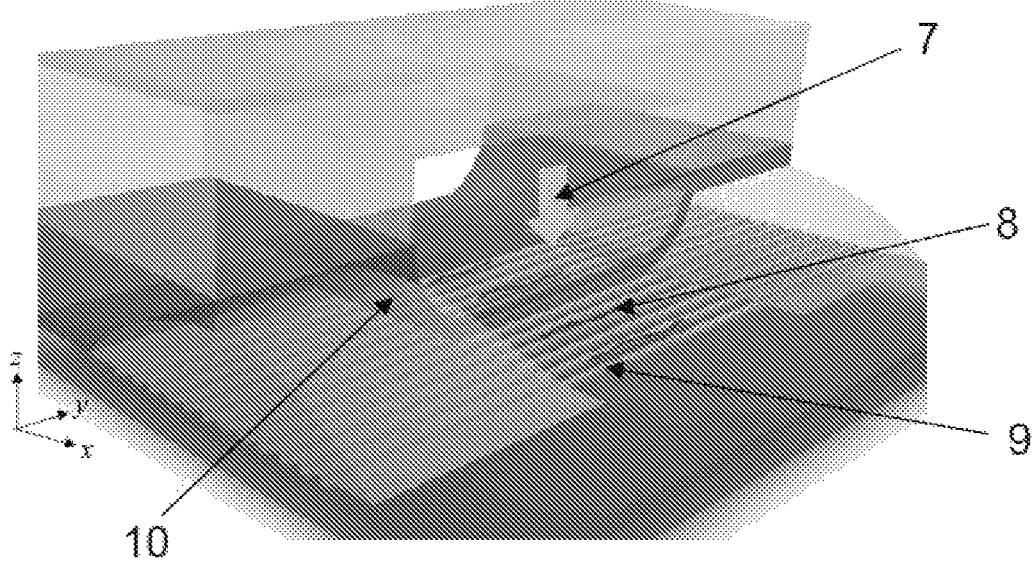
FIG. 1B shows a schematic view of dynamically formed nanochannels when pressure is applied, according to an embodiment of the subject invention. DNA molecules can be stretched in the created nanochannels, and a smooth gradient interface can be generated between the nanochannels and the adjoining microchannels.
Figure 1C:
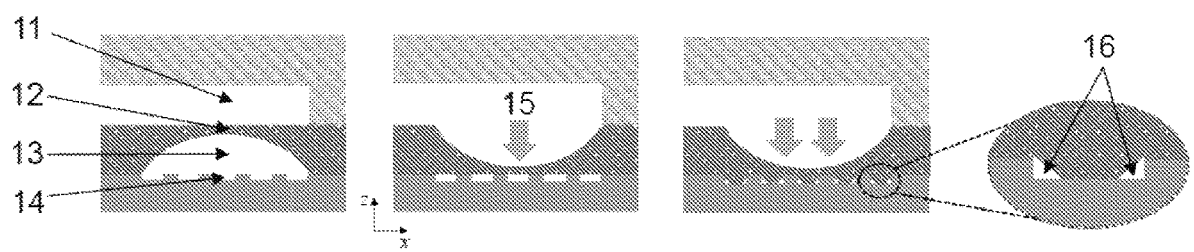
FIG. 1C shows a cross-sectional view of formation of triangular nanochannels by roof collapse of the interlayer, according to an embodiment of the subject invention.

FIG. 1A shows a schematic view of DNA solution transport in recovered microchannels when the interlayer is not deformed, according to an embodiment of the subject invention; FIG. 1B shows a schematic view of dynamically formed nanochannels when pressure is applied, according to an embodiment of the subject invention; and FIG. 1C shows a cross-sectional view of formation of triangular nanochannels by roof collapse of the interlayer, according to an embodiment of the subject invention. Referring to FIG. 1B, DNA molecules can be stretched in the created nanochannels, and a smooth gradient interface can be generated between the nanochannels and the adjoining microchannels. Referring to FIGS. 1A and 1B, coiled DNA 4 can be stretched and linearized in the nanochannels by application of control pressure 7 (e.g., by one or more pneumatic valves, such as pneumatic microvalves), resulting in a stretched DNA molecule 8. FIGS. 1A and 1B also show the control microchannel 1, the interlayer 2, the sample microchannel 4, the nanoslits 5, the substrate 6 (e.g., rigid substrate), a collapsed nanoslit 9, and the smooth gradient 10 between the microchannel 3 and the nanochannels.

When confined in a nanochannel, a coiled DNA molecule can stretch out as a combined result of the excluded volume effect and its elastic properties, depending on the dimensions of the nanochannel. Compared with other approaches, DNA stretching by nanoconfinement allows a uniform stretch where the confined DNA molecule is exposed to the same confinement force and provides a long amount of time for observation of DNA in its stretched state. By parallelizing the nanochannels and coupling them with microfluidics, tens and hundreds of prolonged DNA molecules can be analyzed simultaneously, allowing rapid acquisition of statistics, high reproducibility, and easy automation.

Referring to FIG. 1C, control pressure 15 can be applied over the one or more nanoslits 14 leading to collapsed nanoslits 16 for DNA stretching, which can each have a triangular cross-section (see right-hand section of FIG. 1C). Also shown in FIG. 1C are the control microchannel 11, the interlayer 12, and the sample microchannel 13.

Figure 2A:
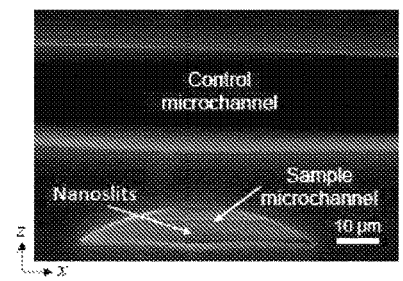
FIG. 2A shows a scanning electron microscope (SEM) image of a cross section of a device according to an embodiment of the subject invention.
Figure 2B:
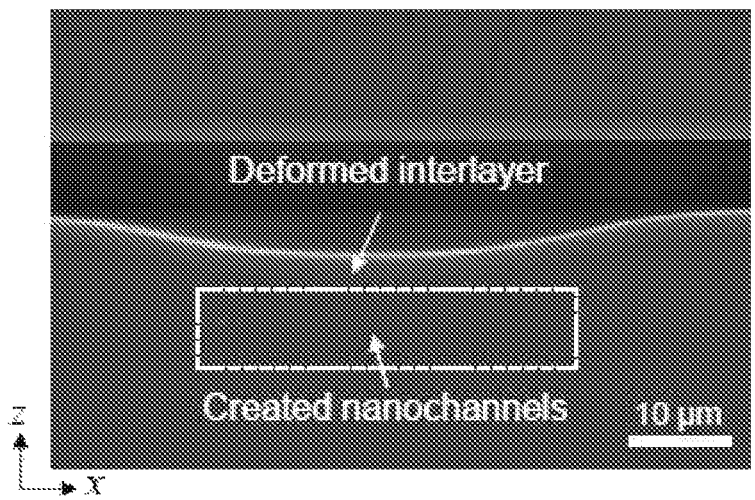
FIG. 2B shows an SEM image of a cross section of a deformed interlayer according to an embodiment of the subject invention.
Figure 2C:
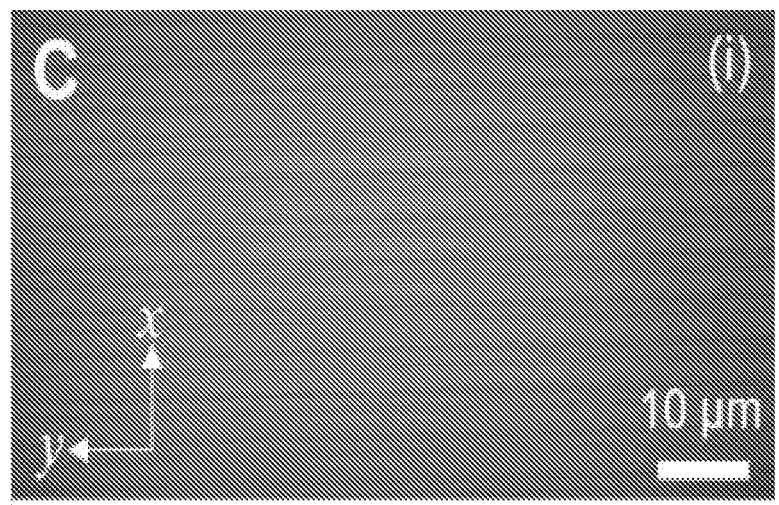
FIG. 2C shows a microscopic image of nanoslits before compression.
Figure 2D:
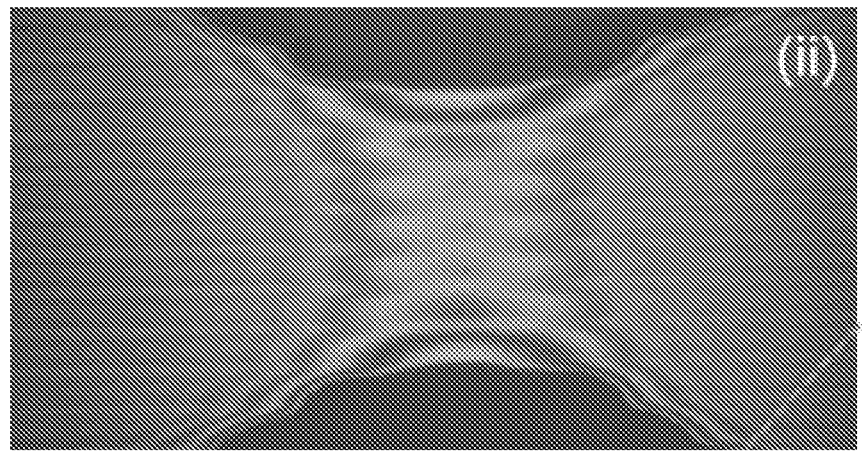
FIG. 2D shows a microscopic image of the nanoslits shown in FIG. 2C during compression, illustrating the collapse process according to an embodiment of the subject invention.
Figure 2E:
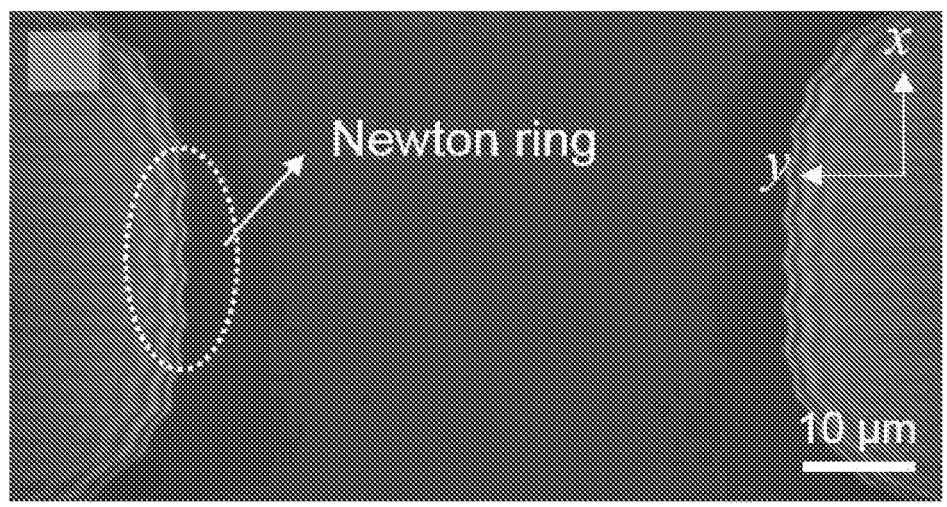
FIG. 2E shows a microscopic image of the nanoslits shown in FIGS. 2C and 2D after compression, illustrating the collapse process (in combination with FIGS. 2C and 2D) according to an embodiment of the subject invention. The curved edges of the microvalve indicate gradual change in height between the nanochannels and the adjoining microchannels.
Figure 2F:
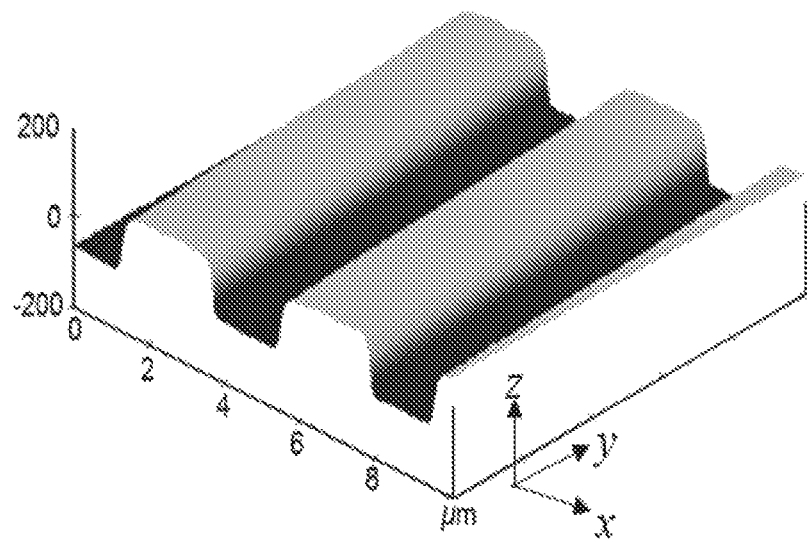
FIG. 2F shows an atomic force microscope (AFM) image of nanoslits on a substrate according to an embodiment of the subject invention.
Figure 2G:
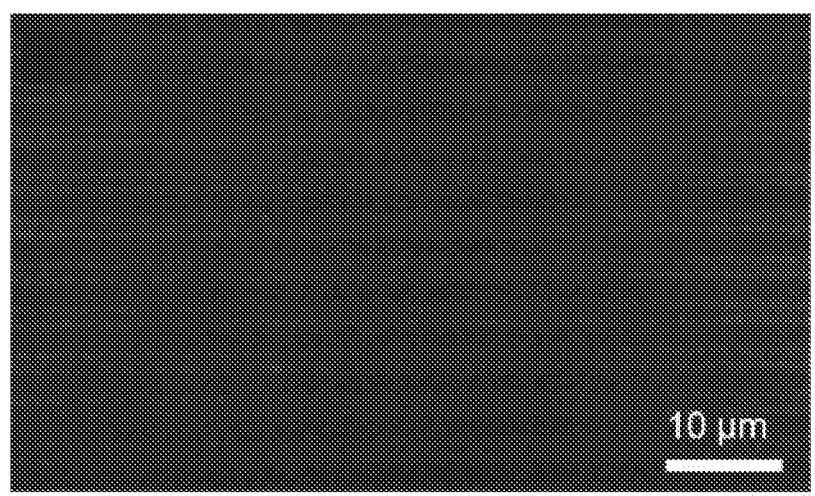
FIG. 2G shows a fluorescent view of formed nanochannel, showing uniformity, of a device according to an embodiment of the subject invention.
Figure 3:
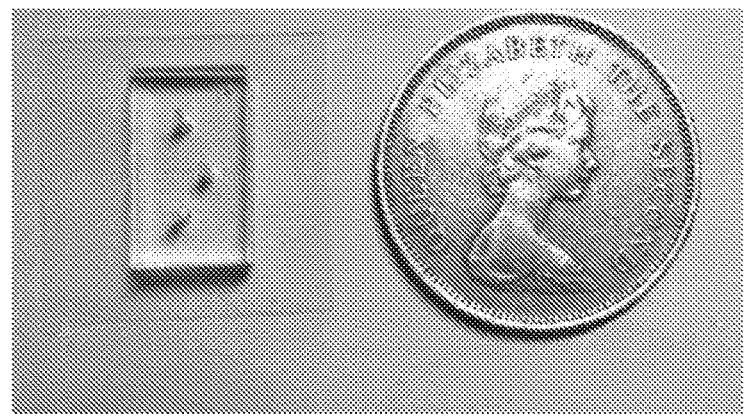
FIG. 3 shows an image of a nanofluidic chip according to an embodiment of the subject invention; a coin that is approximately the size of a U.S. quarter is shown for size comparison.

FIG. 2A shows a scanning electron microscope (SEM) image of a cross section of a device according to an embodiment of the subject invention, and the nanoslits can be seen at the bottom portion. FIG. 2B shows an SEM image of a cross section of a deformed interlayer according to an embodiment of the subject invention; FIG. 2C shows a microscopic image of nanoslits before compression; FIG. 2D shows a microscopic image of the nanoslits shown in FIG. 2C during compression, illustrating the collapse process according to an embodiment of the subject invention; and FIG. 2E shows a microscopic image of the nanoslits shown in FIGS. 2C and 2D after compression, illustrating the collapse process (in combination with FIGS. 2C and 2D) according to an embodiment of the subject invention. The curved edges of the microvalve indicate gradual change in height between the nanochannels and the adjoining microchannels. FIG. 2F shows an atomic force microscope (AFM) image of nanoslits on a substrate according to an embodiment of the subject invention; and FIG. 2G shows a fluorescent view of formed nanochannel, showing uniformity, of a device according to an embodiment of the subject invention.

Embodiments of the subject invention can be used in, for example, biochip-based diagnostics instruments for genetic/ epigenetic research, quick screening of diseases, and forensic criminal investigation. Instead of DNA sequencing or polymerase chain reaction (PCR) amplification, single-molecule DNA profiling offers a quick detection of bio-markers such as DNA methylation patterns and large genomic rearrangements (repetitive or deleted patterns) for diagnosis of inherited disorders and diseases, monitoring response to drug treatments, and forensic identification.

In some embodiments, surface treatment can be performed on the substrate (e.g., deformable polymer such as PDMS) to enhance the long-term stability of the substrate.

In certain embodiments, a nanofluidic device as described herein can be coupled with a single cell manipulation module as a platform for single-cell whole genomic analysis. This can be combined with any other features described herein. In some embodiments, a nanofluidic device as described herein can be coupled with super-resolution microscopy to achieve 100 bp (base pair) optical mapping resolution. This can be combined with any other features described herein.

Embodiments of the subject invention include novel platforms to confine and align DNA molecules in dynamically formed nanochannels for optical analysis. By judiciously exploiting the microvalve control and the deformation of nanoslits made in the deformable substrate (e.g., a deformable polymer such as PDMS), submillimeter-long uniform nanochannels can be formed with the effective confining dimension down to 10 or 20 nm using low-cost soft lithography. Referring again to FIGS. 1A-1C, DNA molecules 4 can be initially loaded into the sample microchannel 3 with nanoslits 5 on the bottom. To form a nanoconfinement environment, the interlayer 2 can be gradually pressed into contact with the nanostructured bottom layer by increasing the pressure 7 in the upper control microchannel 1. The extension of the DNA molecules can be tuned by adjusting the confinement imposed from above. When the applied pressure 7 is strong enough, the deformed interlayer 2 will totally collapse in the center of each nanoslit 5, creating triangular collapsed nanoslits 9 or nanochannels. Compared with classical circular or rectangular nanochannels of the same effective size, the triangular nanoslit/nanochannels enhance the extension of DNA due to the entropic depletion in the corners and therefore suppress the thermal fluctuations and back-folding. The curved edge of the microvalve can smoothly bridge the different length scales by more than 3 orders of magnitude between the stretching nanochannels and the adjoining microchannels, facilitating the introduction of DNA into the nanochannels and obviating the need for high pressure or electric fields (see also FIGS. 2A-2G). Unlike related art direct-bonded nanochannels, the sample channel can recover in microscale when the pressure is released. Therefore, the device can be easily flushed without clogging. In addition, surface passivation can be conveniently conducted to suppress the nonspecific interactions on the channel surfaces.

Bacterial infection is a common cause of diseases, such as tuberculosis and meningitis. Identifying the causative agent of the infection at an early stage is crucial. A precise diagnosis is particularly important when antibiotics are used, because inappropriate use of antibiotics has helped create strains of antibiotic resistant bacterium. Apart from diagnosis based on symptoms, conventional methods for identifying bacteria include amplification of bacterial DNA in vitro by PCR and biochemical tests, which are expensive and time consuming. DNA optical mapping in nanochannels according to embodiments of the subject invention has the potential to speed up the diagnosis and enhance the sensitivity while keeping the costs low.

Figure 9:
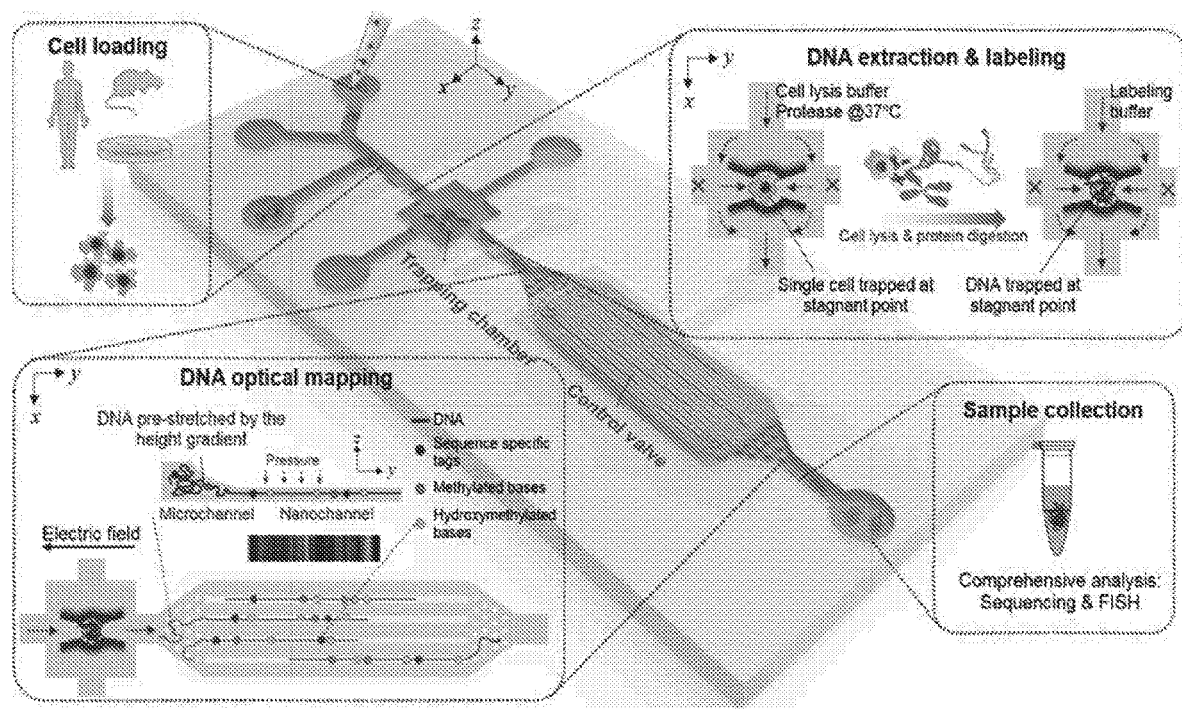
FIG. 9 shows a schematic view of a hybrid micro/nanofluidic platform for single-cell whole genomic analysis according to an embodiment of the subject invention. A specific cell of interest can be microfluidically isolated from a population and trapped in the trapping chamber. Next, intact DNA molecules can be extracted, purified, and labeled. Then, the DNA molecules can be introduced into the dynamic nanochannels for optical mapping. The DNA molecules can then be recovered and collected for sequencing and/or FISH (fluorescent in situ hybridization) detection.

Base-by-base sequencing, as the gold standard in DNA analysis, can provide single nucleotide resolution on a genomic scale, but repetitive sequences cannot be detected by the related art sequencing technology because the DNA is fragmented into short pieces. Fluorescence in situ hybridization (FISH) can resolve large-scale genetic information on intact chromosomes. However, the resolution is limited to 1-10 Mb set by the condensed state of DNA. Optical mapping of a single DNA molecule according to embodiments of the subject invention, on the other hand, bridges the gap between the bird's-eye view of cytogenetics and the worm's-eye view of next generation sequencing. By coupling optical mapping with conventional genomic analysis techniques including DNA sequencing and FISH, a comprehensive single-cell genomic analysis is realized. In an embodiment, a lab-on-a-chip single-cell device can include a cell manipulation module for cell trapping, lysis, DNA extraction, and purification, and a dynamic nanofluidic module for DNA optical mapping. This is shown in FIG. 9. The cell can first be loaded in the micro/nanofluidic lab-on-chip device, and in situ lysed. The DNA molecules can be extracted, purified, and pre-stretched. Then, the DNA molecules can be stretched in the dynamically formed nanochannels, ready for optical mapping. After collecting the rescued DNA, the sample can be amplified for further complementary analysis, including sequencing and FISH. This technique can allow for direct analysis of molecules extracted from a single cell. The genetic variation of all length scales would be detected.

Many cancers exhibit large genomic rearrangements, including for example lung cancer, ovarian cancer, and breast cancer. An early detection of the genomic mutations allows for efficient therapy before the real appearance of tumors. Though next generation sequencing can detect the single nucleotide variant (SNV), the large genomic rearrangements may escape from the current sequencing technology. FISH, as a common tool for cancer diagnosis in clinics, can detect large genomic rearrangements, but its resolution is limited to 1-10 Mb because the DNA is in the condensed state. In an embodiment of the subject invention, by untangling the DNA in the nanofluidic platform and comparing the optical mapping barcode with a standard database, the genomic rearrangements including insertion, deletion, and duplication can be detected with higher resolution. In this way, the efficiency and sensitivity for cancer prediction and assessment can be largely enhanced.

Figure 4:
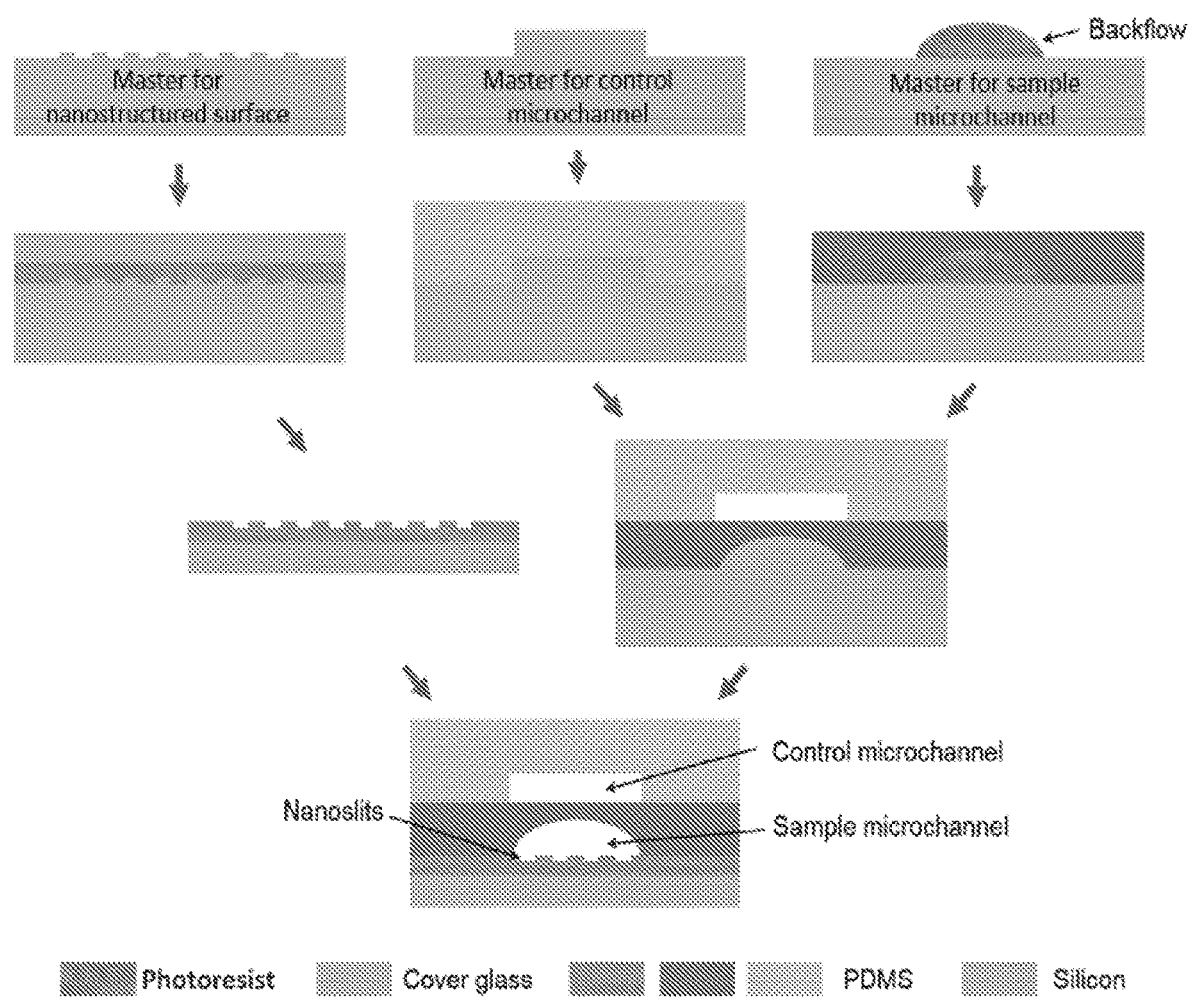
FIG. 4 shows cross-sectional views of process flow for fabricating a nanofluidic device by multilayer soft-lithography, according to an embodiment of the subject invention.
Figure 6:
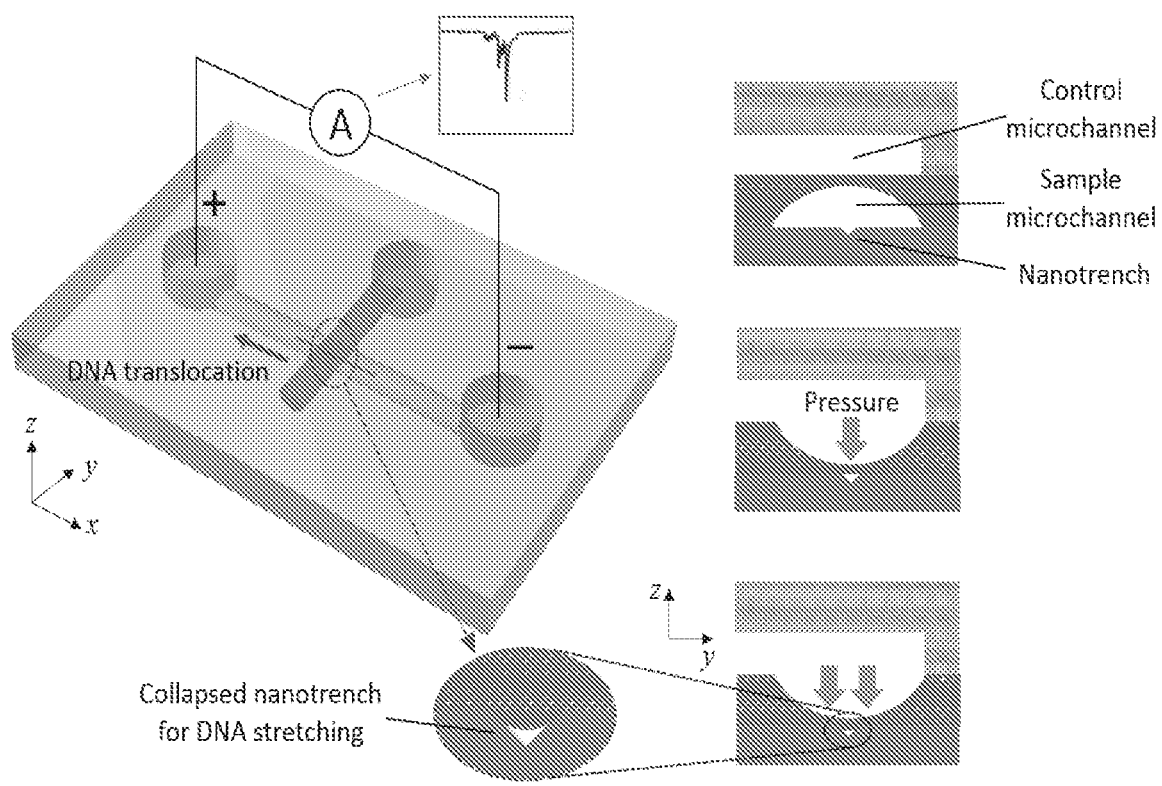
FIG. 6 shows a schematic view (left-hand side of Figure) of a device for modulating DNA translocation in a single nanochannel according to an embodiment of the subject invention. The system can include a microvalve and a sample microchannel with a single nanotrench on the bottom surface. One or more (e.g., two) electrodes can be inserted into the reservoirs for applying a voltage and collecting ionic current. Also shown on the right-hand side of the Figure are cross-sectional views showing that the effective size of the generated nanotrench can be reduced by increasing the applied pressure in the control microchannel to slow down the DNA translocation.

FIG. 4 shows cross-sectional views of process flow for fabricating a nanofluidic device by multilayer soft-lithography, according to an embodiment of the subject invention. Referring to FIG. 4, a master for the nanostructured surface, a master for a control microchannel, and/or a master for a sample microchannel can be used. A substrate layer, which can be a deformable substrate (e.g., a deformable polymer such as PDMS) can be used. A cover glass can also be present as an additional, non-deformable substrate. It is noted that, although "photoresist", "cover glass", "PDMS", and "silicon" are used as labels for the various layers in FIG. 4, this is done for exemplary purposes only, and these layers can be other materials as well. The "cover glass" can be any rigid substrate, the "PDMS" can be any deformable substrate or layer, and the "silicon" can be any semiconductor material or metal. As depicted in the bottom section of FIG. 4, the "cover glass" is the bottom layer, and then three layers of "PDMS" are stacked on the "cover glass". The control microchannel is under the top layer, the sample microchannel is under the second layer from the top, and the nanoslits are formed in the base layer (also referred to herein as deformable substrate or substrate layer). As depicted in FIG. 4, the upper-right-hand cross-section and the section below that includes the curved section that is "photoresist". Each "master" section can be "silicon" or an equivalent material. The bottom material in seven cross-sections depicted in FIG. 4 (the top three, the three in the second row, and the right-hand one in the third row from the top) is "silicon". The "cover glass" is shown in the left-hand-most section in the second and third rows as depicted in FIG. 4, and the stepped layer in each of these sections is "PDMS". FIG. 6 shows a schematic view (left-hand side of Figure) of a device for modulating DNA translocation in a single nanochannel according to an embodiment of the subject invention. The system can include a microvalve and a sample microchannel with a single nanotrench on the bottom surface. One or more (e.g., two) electrodes can be inserted into the reservoirs for applying a voltage and collecting ionic current. Also shown on the right-hand side of the Figure are cross-sectional views showing that the effective size of the generated nanotrench can be reduced by increasing the applied pressure in the control microchannel to slow down the DNA translocation.

Figure 7A:
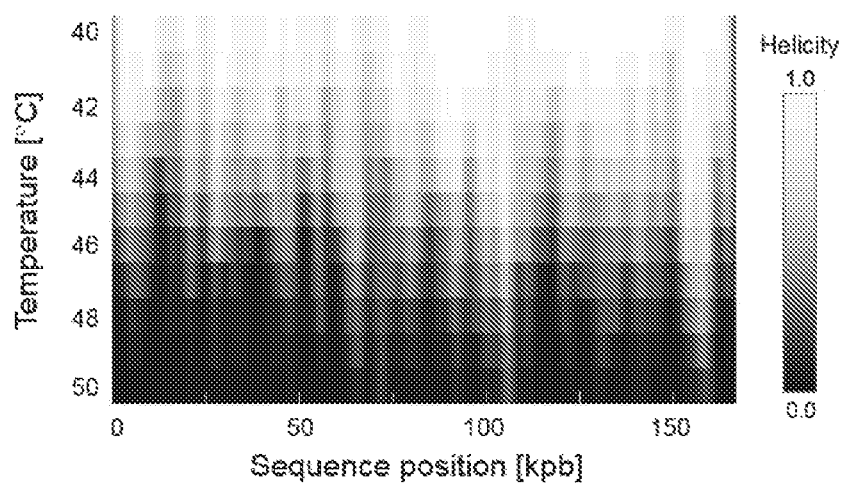
FIG. 7A shows a theoretical melting profile of T4GT7 DNA denaturation optical mapping in a dynamic nanofluidic device according to an embodiment of the subject invention.
Figure 7B:
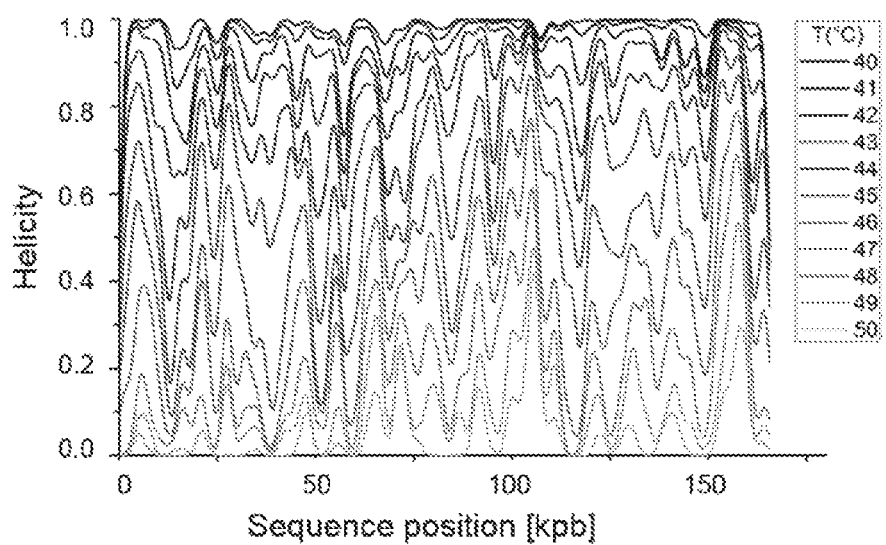
FIG. 7B shows a helicity profile of T4GT7 DNA sequence for DNA denaturation optical mapping in a dynamic nanofluidic device according to an embodiment of the subject invention.
Figure 7C:
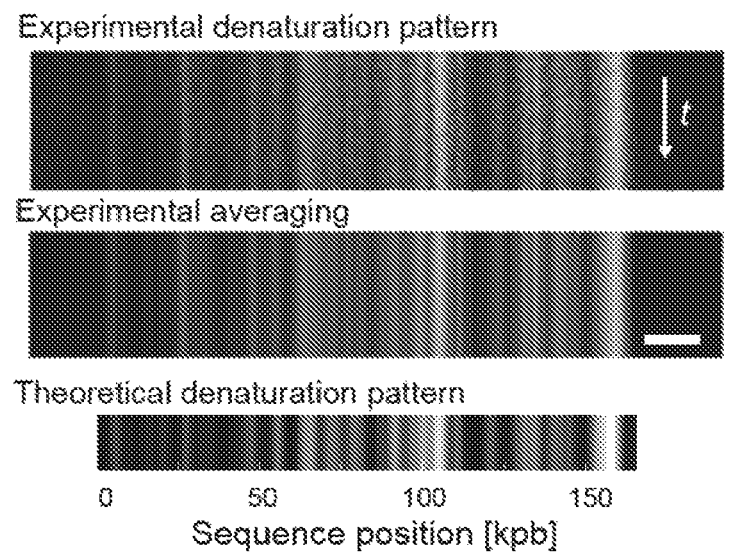
FIG. 7C shows an experimental kymograph and an experimental averaging kymograph for T4GT7 DNA denaturation optical mapping in a dynamic nanofluidic device according to an embodiment of the subject invention, along with a theoretical denaturation pattern (kbp=kilo-base pairs). The scale bar is 5 μm.
Figure 7D:
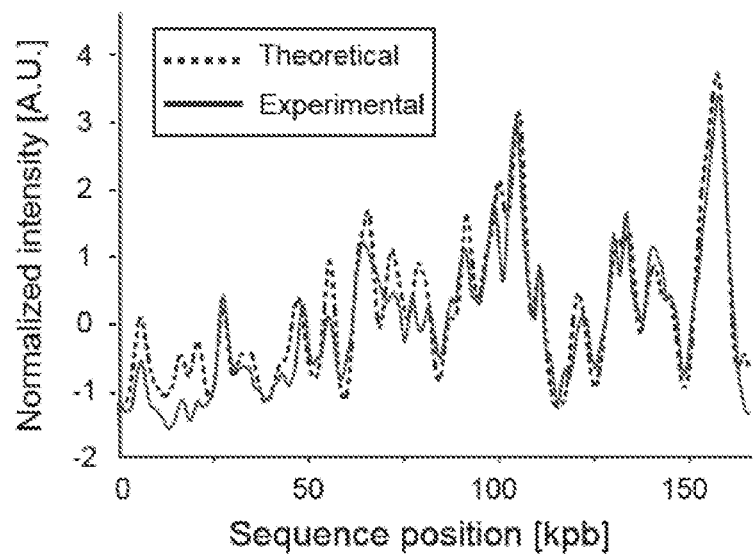
FIG. 7D shows a plot of experimental (solid line) and theoretical (dotted line) normalized intensity versus sequence position for DNA denaturation optical mapping in a dynamic nanofluidic device according to an embodiment of the subject invention.
Figure 8A:
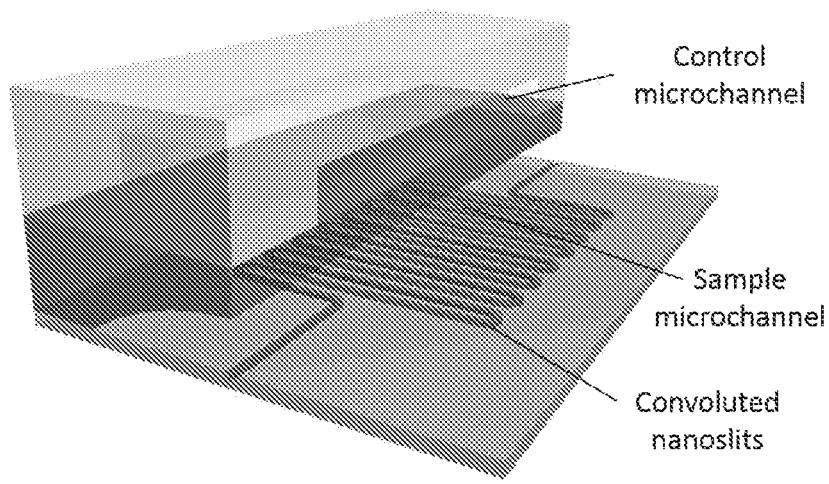
FIG. 8A shows a schematic view of convoluted dynamic nanochannels for ultra-long DNA analysis in a device according to an embodiment of the subject invention.
Figure 8B:
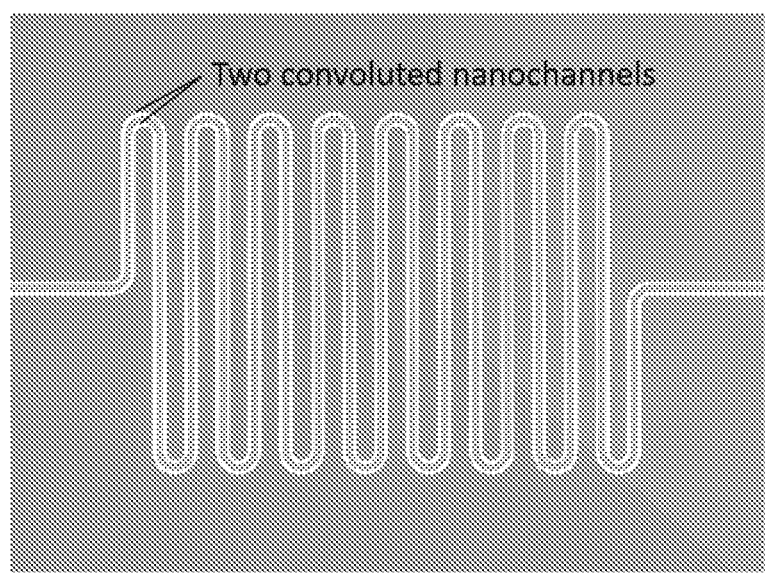
FIG. 8B shows a top view of a convoluted nanoslit deformed into two convoluted nanochannels at the edges in a device according to an embodiment of the subject invention. The stretched long DNA molecules can be directly analyzed with two-dimensional area detectors (e.g., a charge coupled device (CCD)) in a single field of view.

FIG. 7A shows a theoretical melting profile of DNA denaturation optical mapping in a dynamic nanofluidic device according to an embodiment of the subject invention; FIG. 7B shows a helicity profile of T4GT7 DNA sequence for DNA denaturation optical mapping in a dynamic nanofluidic device according to an embodiment of the subject invention; and FIG. 7C shows an experimental kymograph and an experimental averaging kymograph for DNA denaturation optical mapping in a dynamic nanofluidic device according to an embodiment of the subject invention, along with a theoretical denaturation pattern (kbp=kilo-base pairs). The scale bar is 5 FIG. 7D shows a plot of experimental (solid line) and theoretical (dotted line) normalized intensity versus sequence position for DNA denaturation optical mapping in a dynamic nanofluidic device according to an embodiment of the subject invention. FIG. 8A shows a schematic view of convoluted dynamic nanochannels for ultra-long DNA analysis in a device according to an embodiment of the subject invention, and FIG. 8B shows a top view of a convoluted nanoslit deformed into two convoluted nanochannels at the edges in a device according to an embodiment of the subject invention. The stretched long DNA molecules can be directly analyzed with two-dimensional area detectors (e.g., a charge coupled device (CCD)) in a single field of view.

FIG. 9 shows a schematic view of a hybrid micro/nanofluidic platform for single-cell whole genomic analysis according to an embodiment of the subject invention. Referring to FIG. 9, a specific cell of interest can be microfluidically isolated from a population and trapped in the trapping chamber. Next, intact DNA molecules can be extracted, purified, and labeled. Then, the DNA molecules can be introduced into the dynamic nanochannels for optical mapping. The DNA molecules can then be recovered and collected for amplification and/or sequencing.

Figure 10:
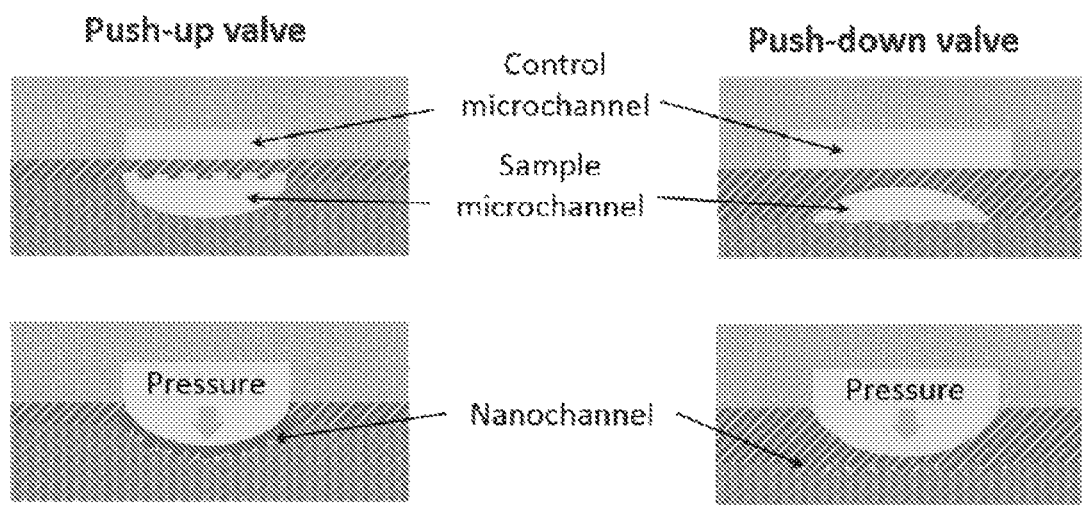
FIG. 10 shows a schematic view of a push-up valve (left-hand side) and a push-down valve (right-hand side) according to an embodiment of the subject invention. The push-up valve can create nanochannels on the semicircular roof of the sample microchannel. The push-down valve can create nanochannels on the planar bottom of the sample microchannel, facilitating the observation of parallel DNA molecules on a planar surface.

FIG. 10 shows schematic view of a push-up valve (left-hand side) and a push-down valve (right-hand side) according to an embodiment of the subject invention. The push-up valve can be fully sealed if the control pressure is high enough. The membrane must be optimized for the push-down valve; if the membrane is too thin or too soft, it will collapse at the center first and will not close on the edges, and if the membrane is too thick or too hard, a very high pressure will be required for sealing.

The subject invention includes, but is not limited to, the following exemplified embodiments.

Embodiment 1

A device for DNA analysis, comprising:
a deformable base layer having at least one nanoslit, with a depth of 900 nanometer (nm) or less (and optionally a length of less than 1 millimeter (mm) and/or a width of 1 micron or more), formed therein in a channel region thereof; and
an interlayer disposed on the base layer such that a sample microchannel is formed between a portion of the interlayer and the channel region of the base layer,
wherein the device is configured such that, when pressure is applied to the interlayer, the interlayer is forced into the at least one nanoslit and makes contact with a bottom surface thereof, thereby forming nanochannels within the nanoslit.

Embodiment 2

The device according to embodiment 1, wherein each nanochannel has a triangular cross-section when viewed lengthwise.

Embodiment 3

The device according to any of embodiments 1-2, wherein the base layer is a deformable polymer.

Embodiment 4

The device according to embodiment 3, wherein the base layer is polydimethylsiloxane (PDMS).

Embodiment 5

The device according to any of embodiments 1-4, wherein the interlayer is a deformable polymer.

Embodiment 6

The device according to embodiment 5, wherein the interlayer is PDMS.

Embodiment 7

The device according to any of embodiments 1-6, further comprising a control layer disposed on the interlayer, wherein the control layer has a control microchannel formed therein between a portion of the control layer and a portion of the interlayer.

Embodiment 8

The device according to embodiment 7, wherein the control layer is a deformable polymer.

Embodiment 9

The device according to embodiment 8, wherein the control layer is PDMS.

Embodiment 10

The device according to any of embodiments 1-9, further comprising a rigid substrate disposed under the base layer.

Embodiment 11

The device according to embodiment 10, wherein the rigid substrate is a cover glass.

Embodiment 12

The device according to any of embodiments 1-11, wherein the depth of the at least one nanoslit is 100 nm or less.

Embodiment 13

The device according to any of embodiments 1-11, wherein the depth of the at least one nanoslit is 50 nm or less.

Embodiment 14

The device according to any of embodiments 1-11, wherein the depth of the at least one nanoslit is 30 nm or less.

Embodiment 15

The device according to any of embodiments 1-11, wherein the depth of the at least one nanoslit is 20 nm or less.

Embodiment 16

The device according to any of embodiments 1-11, wherein the depth of the at least one nanoslit is in a range of from 10 nm to 20 nm.

Embodiment 17

The device according to any of embodiments 1-11, wherein the depth of the at least one nanoslit is 20 nm.

Embodiment 18

The device according to any of embodiments 1-11, wherein the base layer comprises a plurality of nanoslits formed therein in the channel region thereof, each nanoslit having a depth of 900 nm or less (and optionally a length of less than 1 mm and/or a width of 1 micron or more).

Embodiment 19

The device according to embodiment 18, wherein the depth of each nanoslit is 100 nm or less.

Embodiment 20

The device according to embodiment 18, wherein the depth of each nanoslit is 50 nm or less.

Embodiment 21

The device according to embodiment 18, wherein the depth of each nanoslit is 30 nm or less.

Embodiment 22

The device according to embodiment 18, wherein the depth of each nanoslit is 20 nm or less.

Embodiment 23

The device according to embodiment 18, wherein the depth of each nanoslit is in a range of from 10 nm to 20 nm.

Embodiment 24

The device according to embodiment 18, wherein the depth of each nanoslit is 20 nm.

Embodiment 25

The device according to any of embodiments 18-24, wherein the width and the depth of each nanochannel is the same.

Embodiment 26

The device according to any of embodiments 1-25, wherein the sample microchannel has a dome shape.

Embodiment 27

The device according to any of embodiments 7-26, wherein the control microchannel has a rectangular cross-section when viewed lengthwise.

Embodiment 28

The device according to any of embodiments 7-27, wherein the control microchannel has a length that is the same as that of each nanoslit and a width in a range of 1 micrometer to 900 micrometers.

Embodiment 29

The device according to any of embodiments 1-28, wherein the sample microchannel has a length that is the same as that of each nanoslit and a width in a range of 1 micrometer to 900 micrometers.

Embodiment 30

A method of analyzing DNA utilizing the device according to any of embodiments 1-29, the method comprising:
providing a DNA molecule to the at least one nanoslit; and
applying pressure to an upper surface of the interlayer such that the sample microchannel collapses and the interlayer is forced into the nanoslit, thereby forming nanochannels therein (these steps are not necessarily performed in this order),
wherein the DNA molecule is stretched and linearized within a nanochannel of the nanoslit when the microchannel collapses due to the pressure applied to the interlayer.

Embodiment 31

The method according to embodiment 30, wherein applying pressure to the upper surface of the interlayer comprises pneumatically applying pressure to the upper surface of the interlayer.

Embodiment 32

The method according to embodiment 31, wherein pneumatically applying pressure to the upper surface of the interlayer comprises using a microvalve to pneumatically apply the pressure.

Embodiment 33

The method according to any of embodiments 30-32, further comprising optically mapping the linearized DNA molecule within the nanochannel.

Embodiment 34

The method according to any of embodiments 30-33, further comprising obtaining a denaturation barcode of the DNA molecule.

Embodiment 35

The method according to embodiment 34, further comprising comparing the obtained denaturation barcode to known denaturation barcodes to determine the sequence of the DNA molecule.

Embodiment 36

A method of fabricating a DNA analysis device, the method comprising:
forming a first master template for a nanostructured surface, the first master template having at least one nanoslit formed therein;
forming a second master template for a sample microchannel;

depositing a photoresist material on the second master template;

depositing a first deformable material on the first master template;

removing the first master template from the first deformable material, thereby forming a base layer of the first deformable material having the at least one nanoslit formed therein in a channel region thereof;

depositing a second deformable material on the second master template and the photoresist material;

removing the second master template and the photoresist material from the second deformable material, thereby forming an interlayer of the second deformable material having a sample microchannel formed therein in a shape of the photoresist material; and disposing the interlayer on the base layer such that the at least one nanoslit of the base layer faces the interlayer, and the sample microchannel is disposed facing the base layer and over the channel region of the base layer, wherein the device is configured such that, when pressure is applied to the interlayer, the interlayer is forced into the at least one nanoslit and makes contact with a bottom surface thereof, thereby forming nanochannels within the nanoslit.

Embodiment 37

The method according to embodiment 36, wherein a depth of each nanoslit is 900 nm or less (and optionally a length of each nanoslit is less than 1 mm and/or a width of each nanoslit is 1 micron or more).

Embodiment 38

The method according to any of embodiments 36-37, wherein each nanochannel has a triangular cross-section when viewed lengthwise.

Embodiment 39

The method according to any of embodiments 36-38, further comprising:

forming a third master template for a control microchannel, the third master template having a protrusion thereon;

depositing a third deformable material on the third master template;

removing the third master template from the third deformable material, thereby forming a control layer of the third deformable material having a control microchannel formed therein in a shape of the protrusion; and disposing the control layer on the interlayer such that the control microchannel is formed between the control layer and the interlayer.

Embodiment 40

The method according to any of embodiments 36-39, wherein the first deformable material is a deformable polymer.

Embodiment 41

The method according to embodiment 40, wherein the first deformable material is PDMS.

Embodiment 42

The method according to any of embodiments 36-41, wherein the second deformable material is a deformable polymer.

Embodiment 43

The method according to embodiment 42, wherein the second deformable material is PDMS.

Embodiment 44

The method according to any of embodiments 39-43, wherein the third deformable material is a deformable polymer.

Embodiment 45

The method according to embodiment 44, wherein the third deformable material is PDMS.

Embodiment 46

The method according to any of embodiments 36-45, wherein the first deformable material is the same as the second deformable material.

Embodiment 47

The method according to any of embodiments 39-46, wherein the first deformable material is the same as the third deformable material.

Embodiment 48

The method according to any of embodiments 39-47, wherein the second deformable material is the same of the third deformable material.

Embodiment 49

The method according to any of embodiments 36-48, further comprising disposing a rigid substrate on the first deformable material before removing the first master template from the first deformable material, wherein the rigid substrate remains under the base layer after the interlayer has been disposed on the base layer.

Embodiment 50

The method according to embodiment 49, wherein the rigid substrate is a cover glass.

Embodiment 51

The method according to any of embodiments 36-50, wherein the first master template comprises silicon.

Embodiment 52

The method according to any of embodiments 36-51, wherein the second master template comprises silicon.

Embodiment 53

The method according to any of embodiments 39-52, wherein the third master template comprises silicon.

Embodiment 54

The method according to any of embodiments 36-53, wherein a material of the first master template is the same as that of the second master template.

Embodiment 55

The method according to any of embodiments 39-54, wherein a material of the first master template is the same as that of the third master template.

Embodiment 56

The method according to any of embodiments 39-55, wherein a material of the second master template is the same as that of the third master template.

Embodiment 57

The method according to any of embodiments 36-56, wherein the depth of the at least one nanoslit is 100 nm or less.

Embodiment 58

The method according to any of embodiments 36-56, wherein the depth of the at least one nanoslit is 50 nm or less.

Embodiment 59

The method according to any of embodiments 36-56, wherein the depth of the at least one nanoslit is 30 nm or less.

Embodiment 60

The method according to any of embodiments 36-56, wherein the depth of the at least one nanoslit is 20 nm or less.

Embodiment 61

The method according to any of embodiments 36-56, wherein the depth of the at least one nanoslit is in a range of from 10 nm to 20 nm.

Embodiment 62

The method according to any of embodiments 36-56, wherein the depth of the at least one nanoslit is 20 nm.

Embodiment 63

The method according to any of embodiments 36-56, wherein the base layer comprises a plurality of nanoslits formed therein in the channel region thereof, each nanoslit having a depth of 900 nm or less (and optionally a length of less than 1 mm and/or a width of 1 micron or more).

Embodiment 64

The method according to embodiment 63, wherein the depth of each nanoslit is 100 nm or less.

Embodiment 65

The method according to embodiment 63, wherein the depth of each nanoslit is 50 nm or less.

Embodiment 66

The method according to embodiment 63, wherein the depth of each nanoslit is 30 nm or less.

Embodiment 67

The method according to embodiment 63, wherein the depth of each nanoslit is 20 nm or less.

Embodiment 68

The method according to embodiment 63, wherein the depth of each nanoslit is in a range of from 10 nm to 20 nm.

Embodiment 69

The method according to embodiment 63, wherein the depth of each nanoslit is 20 nm.

Embodiment 70

The method according to any of embodiments 63-69, wherein the width and the depth of each nanochannel is the same.

Embodiment 71

The method according to any of embodiments 36-70, wherein photoresist material is deposited in a dome shape, and wherein the sample microchannel has a dome shape.

Embodiment 72

The method according to any of embodiments 39-71, wherein the protrusion has a rectangular cross-section, and wherein the control microchannel has a rectangular cross-section when viewed lengthwise.

Embodiment 73

The method according to any of embodiments 39-72, wherein the control microchannel has a length that is the same as that of each nanoslit and a width in a range of 1 micrometer to 900 micrometers.

Embodiment 74

The method according to any of embodiments 36-73, wherein the sample microchannel has a length that is the same as that of each nanoslit and a width in a range of 1 micrometer to 900 micrometers.

Embodiment 75

A device for macromolecule analysis, comprising:
a sample microchannel having a cross-section and stiffness configured to allow microchannel collapse with uniform (or approximately uniform) closure;
at least one open nanostructure formed on the roof or bottom surface of the sample microchannel, wherein the at least one open nanostructure has a depth of 100 nm or less; and a control microlayer (e.g., a pneumatic microvalve) disposed above or below the sample microchannel and configured to control collapse of the sample microchannel, an interlayer of the sample microchannel being disposed between the control microchannel and an open portion of the sample microchannel, wherein the device is configured such that, when pressure is applied to the interlayer by the control microchannel, the interlayer is forced into the at least one nanostructure and makes contact with a bottom surface thereof, thereby forming nanochannels within the nanostructure.

Embodiment 76

The device according to embodiment 75, wherein a width of each nanostructure is 1 micron or more.

Embodiment 77

The device according to any of embodiments 75-76, wherein a height of the sample microchannel is in a range of from 5 microns to 50 microns.

Embodiment 78

The device according to any of embodiments 75-77, wherein each nanostructure present is a straight nanoslit, a curved nanoslit, or a nanopit.

Embodiment 79

The device according to any of embodiments 75-78, wherein a width of each nanochannel is 100 nm or less and a depth of each nanochannel is 100 nm or less.

Embodiment 80

The device according to any of embodiments 75-78, wherein a width of each nanochannel is in a range of from 10 nm to 100 nm and a depth of each nanochannel is in a range of from 10 nm to 100 nm.

Embodiment 81

The device according to any of embodiments 75-80, wherein each nanochannel has a triangular cross-section when viewed lengthwise.

Embodiment 82

The device according to any of embodiments 75-81, wherein each nanochannel can be tuned by changing the pressure applied to the interlayer.

Embodiment 83

The device according to any of embodiments 75-82, wherein a length of each nanochannel is in a range of from 10 microns to 10 mm.

Embodiment 84

The device according to any of embodiments 75-83, wherein each nanochannel is configured to handle double-stranded DNA with a contour length in a range of from 50 kbp (kilo-base-pairs) to 1000 Mbp (mega-base-pairs).

Embodiment 85

The device according to any of embodiments 75-83, wherein the device is configured to be used for DNA analysis or protein analysis.

Embodiment 86

The device according to any of embodiments 75-85, wherein each nanochannel is not directly bonded (i.e., is not formed by bonding any portion of the nanostructure to any other portion of the nanostructure) and is capable of recovering to microscale upon release of applied pressure.

Embodiment 87

A method of analyzing DNA or protein utilizing the device according to any of embodiments 75-86, the method comprising:
providing a macromolecule (e.g., DNA or protein) to the at least one nanostructure; and
applying pressure to the interlayer, by the control microchannel, such that the sample microchannel collapses and the interlayer is forced into the at least one nanostructure, thereby forming nanochannels therein (these steps are not necessarily performed in this order),
wherein the macromolecule is stretched and linearized within a nanochannel of the nanostructure when the microchannel collapses due to the pressure applied to the interlayer.

Embodiment 88

The method according to embodiment 87, wherein, when the sample microchannel collapses, a curved edge of the interlayer smoothly bridged different length scales by more than 3 orders of magnitude between the nanochannels for macromolecule stretching and the sample microchannel (thereby facilitating the introduction of macromolecules into the nanochannels and obviating the need for high pressure or electric fields; this smooth transition can largely reduce the entropic barrier between the microchannel and the nanochannels).

Embodiment 89

The method according to embodiment 88, wherein a gradient of the curved edge of the interlayer is configured to be tuned by the pressure applied by the control microchannel, and is also reversible when the pressure is released.

Embodiment 90

The method according to any of embodiments 88-89, wherein the smooth transition bridges length scales from a single cell (on the order of 10 microns) to genomic DNA (on the order of 50 nm) (thereby allowing the device of the method to be used for efficient on-chip cell lysis and downstream DNA analysis).

Embodiment 91

The method according to any of embodiments 87-90, wherein the method is used for on-chip cell lysis or downstream DNA analysis.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

Figure 11:
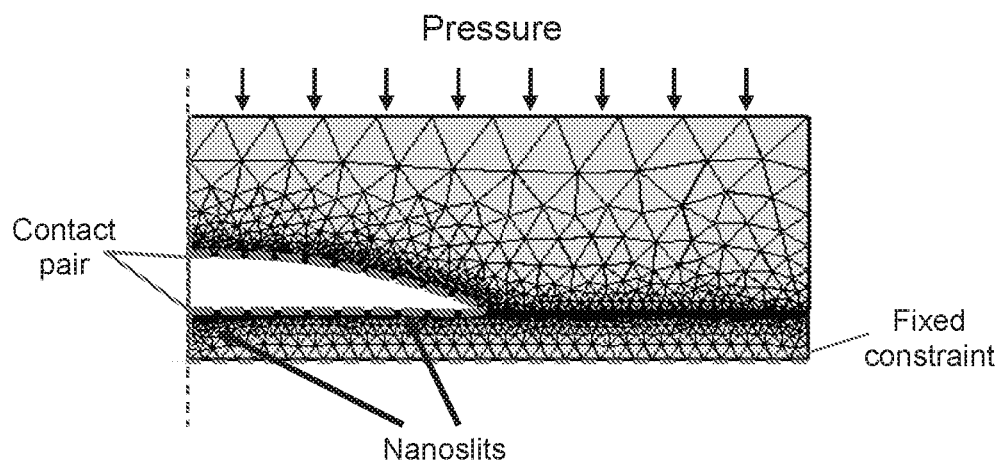
FIG. 11 shows a cross-sectional view of hyper-elastic deformation of the microvalve with nanoslits on the bottom surface of a device according to an embodiment of the subject invention, modeled using finite element modeling (FEM).
Figure 12:
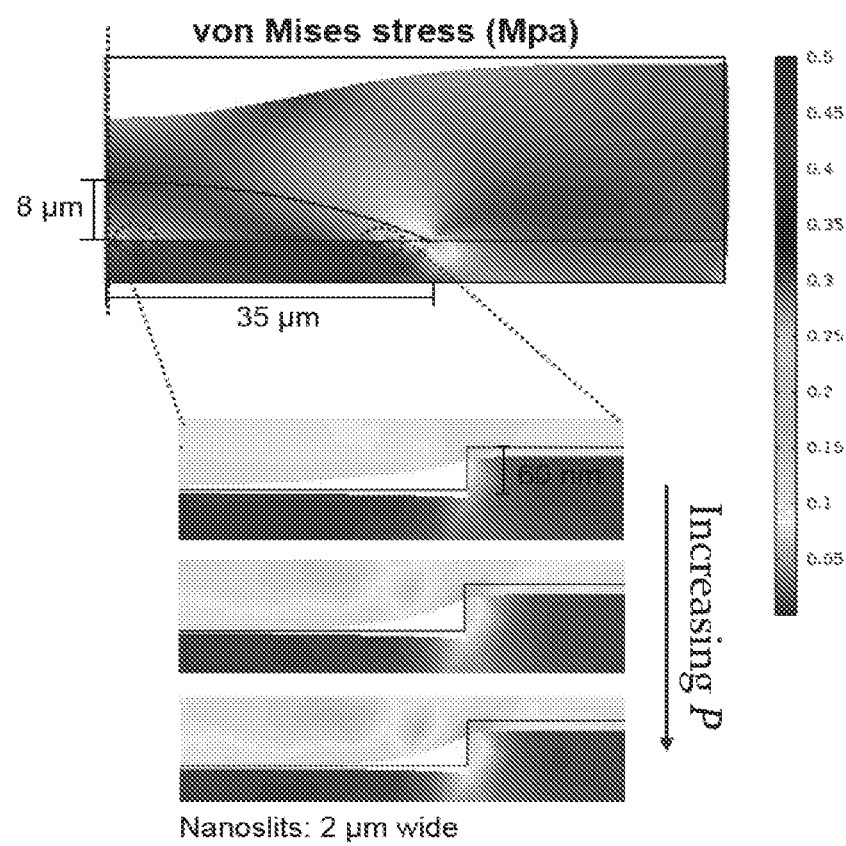
FIG. 12 shows the von Mises stress for the modeled device depicted in FIG. 11.
Figure 13:
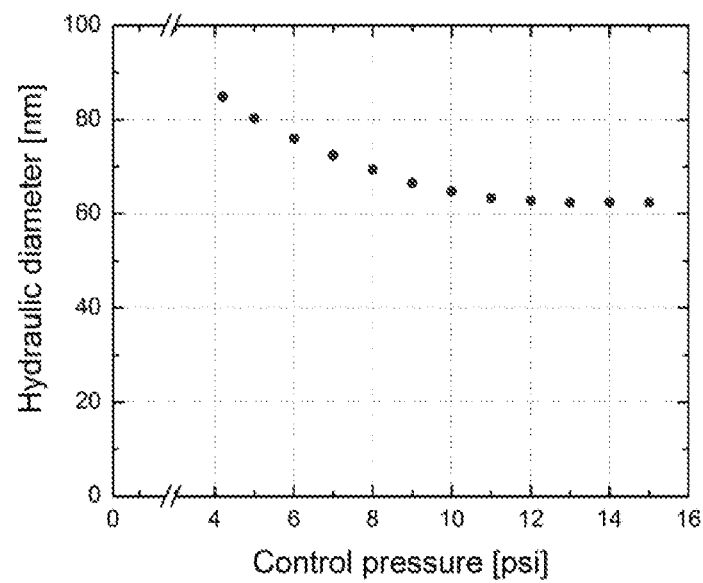
FIG. 13 shows a plot of hydraulic diameter (in nm), $D_H=(4 A)/P$, versus control pressure (in psi) for the modeled device depicted in FIG. 11.

A finite element modeling (FEM) simulation was run on a device as described herein, including nanochannels having nanoslits formed therein by compression of the interlayer. The nanochannels were formed in PDMS and each had a width of about 20 nm and a submillimeter length. FIG. 11 shows a cross-sectional view of hyper-elastic deformation the microvale with nanoslits on the bottom surface of the device, modeled using FEM. FIG. 12 shows the von Mises stress for the modeled device depicted in FIG. 11. FIG. 13 shows a plot of hydraulic diameter (in nm), $D_H=(4\ A)/P$, versus control pressure (in psi) for the modeled device depicted in FIG. 11. Referring to FIG. 13, the hydraulic diameter generally decreases as the control pressure increases.

Example 2

Figure 14:
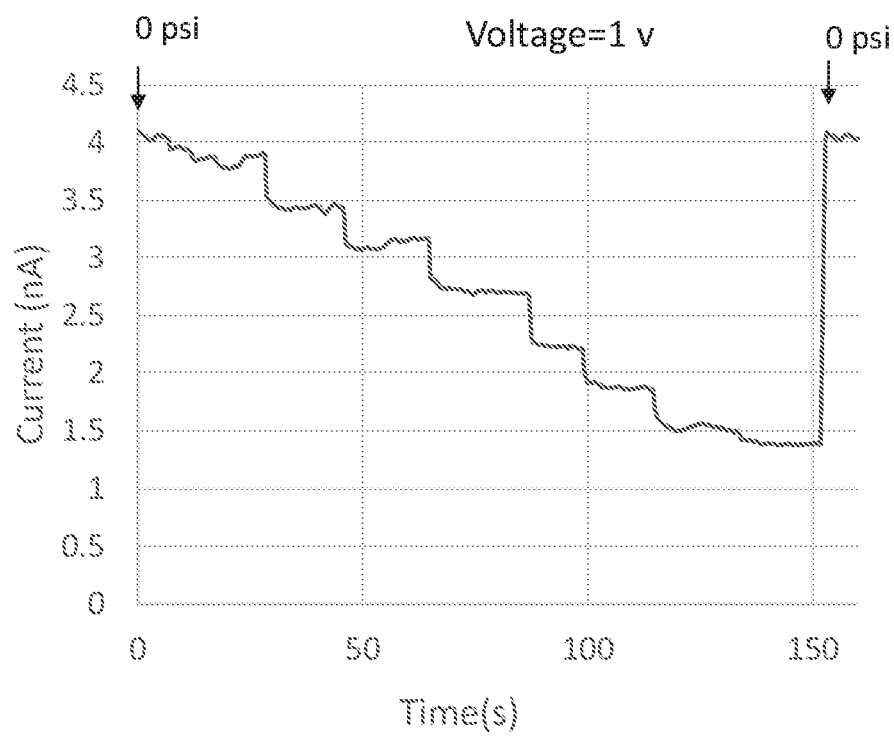
FIG. 14 shows a plot of ionic current (in nA) versus time (in seconds) for a nanochannel according to an embodiment of the subject invention at 1 Volt (V) having the control pressure varied (the various pressures are labeled on the plot). It can be seen that higher pressures lead to lower ionic currents.
Figure 15:
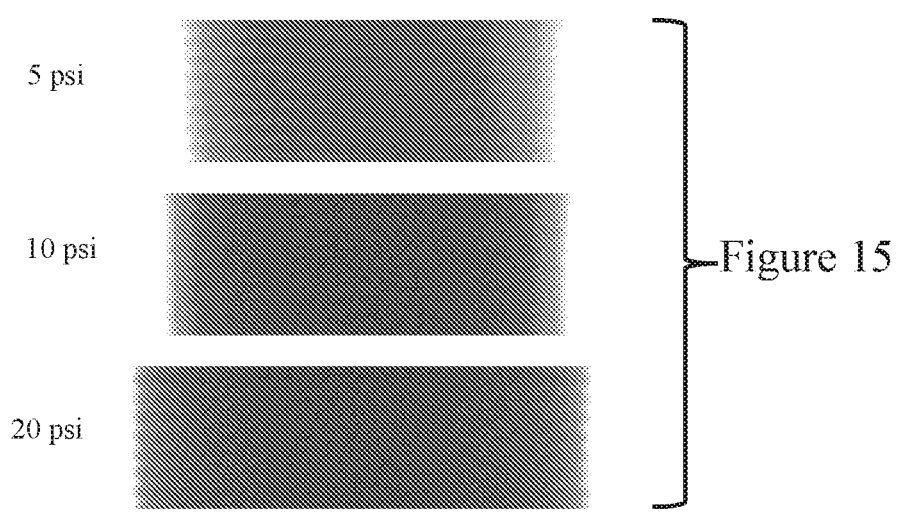
FIG. 15 shows image of the fluorescent intensity of nanochannels of a device according to an embodiment of the subject invention, at pressures of 5 psi (top section), 10 psi (middle section), and 20 psi (bottom section).

Nanochannels were created in PDMS each with a width of about 20 nm and a submillimeter length. The pressure was increased in increments of 5 psi, and the ionic current was measured at different times/pressures in one of the nanochannels. FIG. 14 shows a plot of the ionic current (in nA) versus time (in seconds) for the nanochannel according to an embodiment of the subject invention at a voltage of 1 Volt (V) having the control pressure varied (the various pressures are labeled on the plot). It can be seen that higher pressures lead to lower ionic currents. FIG. 15 shows images of the fluorescent intensity of nanochannels of the device at pressures of 5 psi (top section), 10 psi (middle section), and 20 psi (bottom section).

Example 3

Figure 5A:
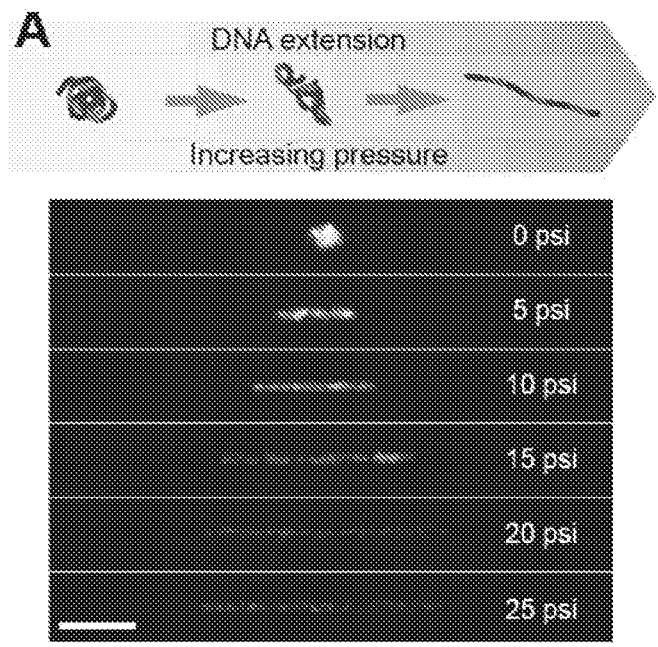
FIG. 5A shows top loading for introducing DNA into nanochannels according to an embodiment of the subject invention. The conformational change of λ-DNA under different control pressures (0 psi, 5 psi, 10 psi, 15 psi, 20 psi, and 25 psi) is also shown in the bottom portion of FIG. 5A. The scale bar at the bottom left-hand portion is 5 μm.

DNA stretching was performed in a device as described herein, with 60-nm-deep nanoslits on the bottom layer. In classical nanofluidic devices, DNA was usually translocated from the adjoining microchannels to the nanochannels by high voltage or pressure. In the devices described herein, the DNA can be introduced into the nanoconfined dimensions either through top loading or side loading. For top loading, the DNA sample was first loaded into the sample microchannel. Then, the control pressure was gradually adjusted to deform the PDMS membrane. As a result, the coiled DNA molecule would gradually stretch out with the decreasing nanoconfinement, as shown in FIG. 5A. With the control pressure at 25 psi, the extension of λDNA in the nanochannel was 16.7 attaining ~78% of its contour length. Compared with conventional rectangular or circular nanochannels with the same effective cross-section area, the triangular nanochannels formed in the device described herein further enhance the extension of DNA due to the entropic depletion in the corners and therefore suppress the thermal fluctuations and back-folding.

Figure 5B:
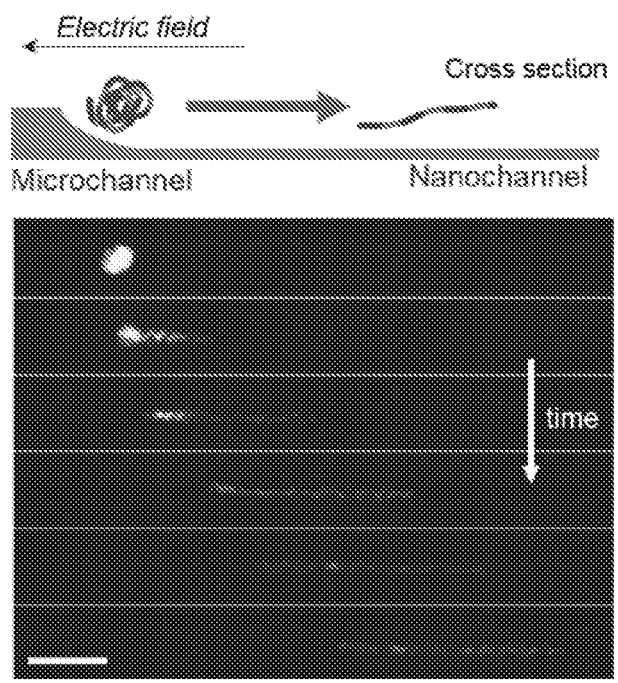
FIG. 5B shows side loading for introducing DNA into nanochannels according to an embodiment of the subject invention. A time trace of λ-DNA translocated from the microchannel by electric pulse and stretched in the nanochannel when the control pressure is applied is also shown in the bottom portion of FIG. 5B. The scale bar at the bottom left-hand portion is 5 μm.

The DNA molecules can also be introduced into the nanochannels by side loading. The control pressure $P_c=15$ psi was first applied to form the nanochannels and the voltage pulse V=500 mV was then applied to trigger the DNA to move from the microchannel into the nanochannels. As shown in FIG. 5B, the curved edge of the microwave smoothly bridged the big barrier between the microchannel and the nanochannel, through which the coiled DNA molecule gradually translocated into the nanochannel and stretched. By utilizing the inherent curved structure generated by the microvalve control, DNA molecules were easily loaded without stacking at the entrance.

Example 4

Denaturation mapping of T4GT7 DNA was performed in a device as described herein, with 60-nm-deep nanoslits on the bottom layer. Along the DNA molecule, the AT-rich regions melt at a lower temperature than the CG-rich regions. When the solution temperature is increased, the YOYO-1 molecules will unbind from the melted regions, creating dark patterns along the DNA molecule while the double stranded regions remain bright. According to the melting possibility of T4GT7 DNA in the solution with 1 mM ionic strength, the theoretical barcodes of different denaturation temperatures were obtained from the calculated helicity profiles by using a Gaussian convolution with standard deviation ~400 nm to simulate the optical broadening. FIGS. 7A and 7B show the varying theoretical denaturation barcodes and the helicity profiles, respectively, ranging from 40° C. to 50° C. The profile variations in FIGS. 7A and 7B qualitatively demonstrate the melting structure and the temperature dependence in the denaturation process.

In the denaturation experiments, the DNA sample in the chip was heated in the water bath for 15 minutes, and then stored in ice to reduce the diffusion and rebind of the free YOYO-1 molecules before the optical detection. Although it is difficult to measure the accurate temperature inside the nanochannels of the chip, the experimental denaturation temperature can be assumed to be close to the water bath temperature due to the sufficient heating time. The experimental intensity profile was compared with the theoretical denaturation maps at different temperatures by using the least-squares alignment procedure to determine the best fit. As shown in FIGS. 7C and 7D, the experimental denaturation barcode shows good agreement with the theoretical calculation.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

1. Eriksson, E., et al., *A microfluidic system in combination with optical tweezers for analyzing rapid and reversible cytological alterations in single cells upon environmental changes*. Lab Chip, 2006. 7(1): p. 71-76.
2. Heller, I., et al., *STED nanoscopy combined with optical tweezers reveals protein dynamics on densely covered DNA*. nAture methods, 2013. 10(9): p. 910-916.
3. Chan, T.-F., et al., *A simple DNA stretching method for fluorescence imaging of single DNA molecules*. Nucleic acids research, 2006. 34(17): p. e113-e113.

4. Otobe, K. and T. Ohtani, *Behavior of DNA fibers stretched by precise meniscus motion control*. Nucleic acids research, 2001. 29(22): p. e109-e109.
5. Labit, H., et al., *A simple and optimized method of producing silanized surfaces for FISH and replication mapping on combed DNA fibers*. BioTechniques, 2009 (45): p. 649-52, 654, 656-8.
6. Bakajin, O., et al., *Electrohydrodynamic stretching of DNA in confined environments*. Physical review letters, 1998. 80(12): p. 2737.
7. Perkins, T. T., D. E. Smith, and S. Chu, *Single polymer dynamics in an elongational flow*. Science, 1997. 276 (5321): p. 2016-2021.
8. Reisner, W., J. N. Pedersen, and R. H. Austin, *DNA confinement in nanochannels: physics and biological applications*. Reports on Progress in Physics, 2012. 75(10): p. 106601.
9. Persson, F., et al., *Confinement spectroscopy: probing single DNA molecules with tapered nanochannels*. Nano letters, 2009. 9(4): p. 1382-1385.
10. Reisner, W., et al., *Statics and dynamics of single DNA molecules confined in nanochannels*. Physical Review Letters, 2005. 94(19): p. 196101.
11. Huh, D., et al., *Tuneable elastomeric nanochannels for nanofluidic manipulation*. Nature materials, 2007. 6(6): p. 424-428.
12. Xu, B.-Y., et al., *Large scale lithography-free nano channel array on polystyrene*. Lab on a Chip, 2010. 10(21): p. 2894-2901.
13. Waits, C. M., A. Modafe, and R. Ghodssi, *Investigation of gray-scale technology for large area 3D silicon MEMS structures*. Journal of Micromechanics and Microengineering, 2003. 13(2): p. 170.
14. Berard, D., et al., *Convex Lens Induced Nanoscale Templating*. Bulletin of the American Physical Society, 2014.
15. Reinhart, W. F., D. R. Tree, and K. D. Dorfman, *Entropic depletion of DNA in triangular nanochannels*. Biomicrofluidics, 2013. 7(2): p. 024102.
16. Min, S. K., et al., *Fast DNA sequencing with a graphene-based nanochannel device*. Nature nanotechnology, 2011. 6(3): p. 162-165.
17. Shendure, J. and H. Ji, *Next-generation DNA sequencing*. Nature biotechnology, 2008. 26(10): p. 1135-1145.
18. Treangen, T. J. and S. L. Salzberg, *Repetitive DNA and next-generation sequencing: computational challenges and solutions*. Nature Reviews Genetics, 2012. 13(1): p. 36-46.
19. Ley, T. J., et al., *DNA sequencing of a cytogenetically normal acute myeloid leukaemia genome*. Nature, 2008. 456(7218): p. 66-72.
20. Levy-Sakin, M. and Y. Ebenstein, *Beyond sequencing: optical mapping of DNA in the age of nanotechnology and nanoscopy*. Current opinion in biotechnology, 2013. 24(4): p. 690-698.
21. Cheeseman, K., et al., *A diagnostic genetic test for the physical mapping of germline rearrangements in the susceptibility breast cancer genes BRCA1 and BRCA2*. Human mutation, 2012. 33(6): p. 998-1009.
22. Lam, E. T., et al., *Genome mapping on nanochannel arrays for structural variation analysis and sequence assembly*. Nature biotechnology, 2012. 30(8): p. 771-776.
23. Persson, F. and J. O. Tegenfeldt, *DNA in nanochannels directly visualizing genomic information*. Chemical Society Reviews, 2010. 39(3): p. 985-999.
24. Reisner, W., et al., *Single-molecule denaturation mapping of DNA in nanofluidic channels*. Proceedings of the National Academy of Sciences, 2010. 107(30): p. 13294-13299.
25. Park, S.-m., et al., *A method for nanofluidic device prototyping using elastomeric collapse*. Proceedings of the National Academy of Sciences, 2009. 106(37): p. 15549-15554.
26. Matsuoka, T., et al., *Nanoscale squeezing in elastomeric nanochannels for single chromatin linearization*. Nano letters, 2012. 12(12): p. 6480-6484.
27. Reisner, W., et al., *Single-molecule denaturation mapping of DNA in nanofluidic channels*. Proceedings of the National Academy of Sciences, 2010. 107(30): p. 13294-13299.
28. Jo, K., et al., *A single-molecule barcoding system using nanoslits for DNA analysis*. Proceedings of the National Academy of Sciences, 2007. 104(8): p. 2673-2678.
29. Mak, A. C., et al., *Genome-Wide Structural Variation Detection by Genome Mapping on Nanochannel Arrays*. Genetics, 2016. 202(1): p. 351-362.
30. Freitag, C., et al., *Visualizing the entire DNA from a chromosome in a single frame*. Biomicrofluidics, 2015. 9(4): p. 044114.
31. Marie, R., et al., *Integrated view of genome structure and sequence of a single DNA molecule in a nanofluidic device*. Proceedings of the National Academy of Sciences, 2013. 110(13): p. 4893-4898.
32. Lam, E. T., et al., *Genome mapping on nanochannel arrays for structural variation analysis and sequence assembly*. Nature biotechnology, 2012. 30(8): p. 771-776.
33. Mahshid, S., et al., *Development of a platform for single cell genomics using convex lens-induced confinement*. Lab on a Chip, 2015. 15(14): p. 3013-3020.
34. Østergaard, P. F., et al., *DNA barcoding via counter-staining with AT/GC sensitive ligands in injection-molded all-polymer nanochannel devices*. Analyst, 2013. 138(4): p. 1249-1255.
35. US20100159462, WO2008134363 Tunable elastomeric nanochannels for nanofluidic manipulation
36. US20120196376, WO2011022650 Nanofilter devices using elastomeric micro to nanochannel interfaces and methods based thereon
37. US20110201509, WO2010042007 Method for the mapping of the local AT/GC ratio along DNA
38. US20110275066, WO2007065025 Method of DNA analysis using micro/nanochannel
39. CA2482566, EP1572860, EP2484751, U.S. Pat. Nos. 7,217,562, 8,333,934, US20140030811, WO2003106693 Gradient structures interfacing microfluidics and nanofluidics, methods for fabrication and uses thereof
40. WO2013088098 Efficient ultra-long DNA analysis in compact nanofluidic channels
41. EP2444157, EP2632592, US20130224736, WO2012055415 Preparation and analysis of samples in micro-/nano-fluidic devices
42. US20140272958, CA2903481, WO2014164739 Nanofluidic devices for the rapid mapping of whole genomes and related systems and methods of analysis
43. US20140206555, CA2454570, EP1417474, WO2003010289 Nanochannel arrays and their preparation and use for high throughput macromolecular analysis.
44. F Persson, et al., Nano Lett, 9(4), 2009.
45. L Menard, et al., Nano Lett, 11(2), 2011.
46. Mills et al., Lab Chip, 10, 1627, 2010.
47. H. Cao. et al., Appl. Phys. Lett., 81(16), (2002).

48. D. J. Berard, et al., PNAS, 111(37), (2014).
49. B. Kim, et al., PhD Thesis, Univ of Mich (2014).
50. U.S. Pat. No. 8,945,909.
51. U.S. Patent Application Publication No. 2010/0159462.
52. E. Angeli, et al., Edorium J Nanotechnol, 1, (2014).
53. I. Fernandez-Cuesta, et al., JVSTB, 29(06F801), (2011).
54. U.S. Patent Application Publication No. 2013/0170026.
55. CA2787242 A1.
56. U.S. Patent Application Publication No. 2007/0161028.
57. M. Napoli. et al., Lab. Chip. 10, 2010.

What is claimed is:

1. A device for DNA analysis, comprising:
a deformable base layer comprising a channel region over which a sample microchannel is disposed;
a plurality of nanoslits, each with a depth of 100 nanometer (nm) or less, formed in the channel region of the base layer, the plurality of nanoslits running in a longitudinal direction of the device; and
an interlayer disposed over the base layer such that the sample microchannel is formed between a central portion of the interlayer and the base layer, the plurality of nanoslits being open to the microchannel,
wherein the interlayer comprises a lower surface facing the plurality of nanoslits and an upper surface opposite to the lower surface,
wherein a cross-section of the upper surface of the interlayer, taken in a latitudinal direction perpendicular to the longitudinal direction, has a flat shape,
wherein the interlayer comprises the central portion and first and second outer portions respectively on either side of the central portion in the latitudinal direction,
wherein a thickness of the central portion of the interlayer, measured in a vertical direction perpendicular to the latitudinal direction and the longitudinal direction, is thinner than that of both the first outer portion of the interlayer and the second outer portion of the interlayer, and
wherein the device is configured such that, when pressure is applied to the upper surface of the central portion of the interlayer, the lower surface of the central portion of the interlayer is forced into the plurality of nanoslits and makes contact with bottom surfaces thereof, thereby reversibly forming nanochannels within the plurality of nanoslits.

2. The device according to claim 1, wherein the base layer is a deformable polymer.

3. The device according to claim 1, wherein the interlayer is a deformable polymer.

4. The device according to claim 1, further comprising a control layer disposed on the interlayer, wherein the control layer has a control microchannel formed therein between a portion of the control layer and a portion of the interlayer.

5. The device according to claim 4, wherein the control layer is a deformable polymer.

6. The device according to claim 4, wherein the control microchannel has a rectangular cross-section when viewed lengthwise.

7. The device according to claim 4, wherein the control microchannel has a length that is the same as that of each nanoslit and a width in a range of 1 micrometer to 900 micrometers.

8. The device according to claim 1, further comprising a rigid substrate disposed under the base layer.

9. The device according to claim 1, wherein each nanoslit has a length in a range of from 10 microns to 10 mm.

10. The device according to claim 9, wherein the length and the depth of each nanochannel is the same.

11. The device according to claim 1, wherein the sample microchannel has a dome shape.

12. The device according to claim 1, wherein the sample microchannel has a length that is the same as that of each nanoslit and a width in a range of 1 micrometer to 900 micrometers.

13. The device according to claim 1, wherein the device is configured such that, when pressure is applied to the interlayer and nanochannels are formed within the plurality of nanoslits, a gradient in depth is also formed between the nanochannels and the sample microchannel.

14. The device according to claim 1, wherein a cross-section of the lower surface of the interlayer, taken in the latitudinal direction, has an arched shape.

* * * * *